(12) United States Patent
Agnew et al.

(10) Patent No.: US 11,771,910 B2
(45) Date of Patent: Oct. 3, 2023

(54) CARDIAC ENERGY HARVESTING DEVICE AND METHODS OF USE

(71) Applicant: The Regents of the University of California, Oakland, CA (US)

(72) Inventors: William J. Agnew, Winchester, CA (US); William C. Tang, Irvine, CA (US); Zachary Siu, Castro Valley, CA (US); Brittanie Chu, Chino Hills, CA (US); Joshua Wang, Northridge, CA (US)

(73) Assignee: The Regents of the University of California, Oakland, CA (US)

( * ) Notice: Subject to any disclaimer, the term of this patent is extended or adjusted under 35 U.S.C. 154(b) by 288 days.

(21) Appl. No.: 17/124,181

(22) Filed: Dec. 16, 2020

(65) Prior Publication Data

US 2021/0178170 A1  Jun. 17, 2021

Related U.S. Application Data

(60) Provisional application No. 62/948,598, filed on Dec. 16, 2019.

(51) Int. Cl.
*A61N 1/37* (2006.01)
*A61N 1/378* (2006.01)
(Continued)

(52) U.S. Cl.
CPC .......... *A61N 1/3785* (2013.01); *A61N 1/362* (2013.01); *A61N 1/3756* (2013.01); *H01F 1/44* (2013.01); *H01F 7/1805* (2013.01); *H01F 38/14* (2013.01); *H02J 7/02* (2013.01); *H02J 50/001* (2020.01); *H02J 50/10* (2016.02); *H02K 1/02* (2013.01); *H02K 1/34* (2013.01); *H02K 35/02* (2013.01); *A61N 1/3787* (2013.01)

(58) Field of Classification Search
CPC ............................ A61N 1/3785; H02K 35/02
See application file for complete search history.

(56) References Cited

U.S. PATENT DOCUMENTS 3,563,245 A   2/1971  McLean
5,941,904 A * 8/1999  Johnston ............ A61N 1/36542
                                                    607/19
(Continued)

OTHER PUBLICATIONS

K. G. Tarakji, C. R. Ellis, P. Defaye, and C. Kennergren, "Cardiac Implantable Electronic Device Infection in Patients at Risk," Arrhythmia Electrophysiol. Rev., vol. 5, No. 1, p. 65, 2016.
(Continued)

*Primary Examiner* — Eric D. Bertram
(74) *Attorney, Agent, or Firm* — Brooks Kushman P.C.

(57) ABSTRACT

A recharging system for recharging batteries or providing power to an implantable device includes an electric coil adapted to be coupled to the implantable device, the electric coil defining a coil interior and a coil exterior. A magnetic component is coupled to the electric coil and adapted to at least partially surround the implantable device. A mechanical actuator is attached to the magnetic component, the mechanical actuator converting compression motion into motion of the magnetic component relative to the electric coil.

17 Claims, 24 Drawing Sheets
(7 of 24 Drawing Sheet(s) Filed in Color)

(51) Int. Cl.
    *H02J 7/02* (2016.01)
    *H02J 50/10* (2016.01)
    *H02J 50/00* (2016.01)
    *H01F 38/14* (2006.01)
    *A61N 1/375* (2006.01)
    *A61N 1/362* (2006.01)
    *H01F 7/18* (2006.01)
    *H02K 1/34* (2006.01)
    *H02K 35/02* (2006.01)
    *H02K 1/02* (2006.01)
    *H01F 1/44* (2006.01)

(56) References Cited

U.S. PATENT DOCUMENTS

| | | | |
|---|---|---|---|
| 6,982,501 | B1 | 1/2006 | Kotha et al. |
| 9,041,230 | B2 | 5/2015 | Arnold et al. |
| 9,590,533 | B2 | 3/2017 | Inman et al. |
| 2004/0222637 | A1* | 11/2004 | Bednyak .......... F03B 13/20 290/1 R |
| 2005/0027332 | A1* | 2/2005 | Avrahami .......... A61N 1/3785 607/61 |
| 2005/0256549 | A1* | 11/2005 | Holzer .......... H02K 35/02 607/35 |
| 2006/0184206 | A1* | 8/2006 | Baker, III .......... H02K 35/06 607/35 |
| 2007/0276444 | A1* | 11/2007 | Gelbart .......... A61N 1/3785 607/6 |
| 2007/0293904 | A1* | 12/2007 | Gelbart .......... A61N 1/3785 607/35 |
| 2009/0171404 | A1* | 7/2009 | Irani .......... A61N 1/056 290/1 R |
| 2009/0171408 | A1* | 7/2009 | Solem .......... A61B 5/1107 607/35 |
| 2012/0059389 | A1* | 3/2012 | Larson .......... G16H 40/67 607/116 |
| 2012/0290043 | A1* | 11/2012 | Gross .......... A61N 1/3785 607/48 |

OTHER PUBLICATIONS

M. A. Karami, D. J. Inman, and M. Amin Karami, "Powering pacemakers from heartbeat vibrations using linear and nonlinear energy harvesters Modeling and experimental verification of a fan-folded vibration energy harvester for leadless pacemakers Powering pacemakers from heartbeat vibrations using linear," Appl. Phys. Lett., vol. 100, No. 101, pp. 42901-41301, 2012.

M. H. Ansari and M. Amin Karami, "Modeling and experimental verification of a fan-folded vibration energy harvester for leadless pacemakers," J. Appl. Phys., vol. 119, No. 100, 2016.

https://www.cdc.gov/dhdsp/data statistics/fact sheets/fs atrial fibrillation. htm.

Afraanz Irani, Mark Bianco, David Tran, Peter Deyoung, Melanie Wyld, Tony Li, 'Energy Generating Systems for Implanted medical Devices' 0171404, 2009.

W. D. Fremont, "Corrosion Resistance and Biocompatibility of Passivated NiTi," 2000.

M. F. Khan, "Design Optimisation for Stent Manufacture," University of Nottingham. Apr. 2018.

K. X. Qian and H. X. Xu, "Gyro-Effect and Earnshaw's Theorem: Stable and Unstable Equilibrium for Rotary and Stationary Permanent Magnetic Levitators," 2008 2nd International Conference on Bioinfomnatics and Biomedical Engineering, Shanghai, 2008, pp. 1323-1325. doi: 10. I 109/ICBBE.2008.659.

Koehler, Kenneth R. College Physics for Students of Biology and Chemistry. Cincinnati, OH: Raymond Walters College University of Cincinnati, 1996: Chapter 3, Fluids: Human Cardiovascular System.

S. Pal, "Design of artificial human joints & organs," Des. Artif. Hum. Joints Organs, vol. 9781461462552, pp. 1-419, 2014.

M. H. Moosavi, N. Fatouraee, H. Katoozian, A. Pashaei, O. Camara, and A. F. Frangi, "Numerical simulation of blood flow in the left ventricle and aortic sinus using magnetic resonance imaging and computational fluid dynamics," Computer Methods in Biomechanics and Biomedical Engineering, vol. 17, No. 7. Taylor & Francis, pp. 740-749, 2014.

V.P. Shastri, "Non-Degradable Biocompatible Polymers in Medicine: Past, Present, Future," Current Pharmaceutical Biotechnology, vol. 4, pp. 331-337, 2003.

* cited by examiner

Where:

k: Spring stiffness
m: Mass
c: Damping coefficient
F(t): Input force
$F_0$: Maximum amplitude of the input force
ω: Input frequency
x(t): Displacement of the mass

| Model | Pictures |
|---|---|
| Solid shell |  |
| Four strip shell |  |

…

CARDIAC ENERGY HARVESTING DEVICE AND METHODS OF USE

CROSS-REFERENCE TO RELATED APPLICATIONS

This application claims the benefit of U.S. provisional application Ser. No. 62/948,598 filed Dec. 16, 2020, the disclosure of which is hereby incorporated in its entirety by reference herein.

TECHNICAL FIELD

In at least one aspect, the present invention relates to medical devices, more specifically to systems and methods for harvesting energy from within the body to extend the operational life of cardiac assistive devices.

BACKGROUND

Pacemakers have evolved in recent years to become small enough to fit inside the ventricle cavities of the heart. This technological feat to minimize the pacemaker design proves to be a significant engineering constraint as it forces the battery pack to be considerably smaller and thus reduces the lifetime of the device from 10 years, standard pacemakers, to 6-7 years. The issue of device longevity has thus become a major point of interest for the biomedical engineering community, especially as a high number of replacement devices fail due to potentially expired battery packs. Doctors installed approximately 1,000,000 implantable cardioverter-defibrillators or pacemakers into patients in 2009, of which about 264,824 of the implanted devices were due to replacements, ~26% of total pacemaker surgeries [1]. Furthermore, the market is primed to shift towards the leadless pacemaker technology as market analysts suggest that there will be large increases in the utilization of ventricular implantable technologies in the near future. Leading the market is Medtronic® and St. Jude Medical® who have begun production of two leadless pacemakers. However, these devices have an average of 6-7 years of lifetime, a reduction from the 10 year lifetime for the standard pacemaker, due to battery constraints that came with the minimal profile of the devices 42 mm×51 mm×6 mm in comparison to 0.8-1 cm3 [2,3]. The question to consider is if this device's lifetime is sufficient for the patient population. Although the average age for pacemaker implantations is 73.5 years old, the number of patients under the age of 65 diagnosed with cardiac arrhythmias is approximately 6.5 million [4]. Thus, if a patient required a pacemaker at a younger age, they have the potential of undergoing multiple replacement surgeries each compounding the patient's risk. The problem statement is thus if battery technologies cannot provide adequate methods to sustain longer device lifetimes, the device must then be designed with a methodology of recharging itself to amplify its longevity.

Energy harvesting is a possible approach for recharging implantable devices. Energy harvesting solutions include using (1) thermal differences, (2) piezo-electric material electromagnetic induction (3) or electromagnetic induction.

However, using thermal differences inside the heart to create energy may not be a viable approach, since the body maintains a nearly constant temperature of 97° F.

With typical electromagnetic induction devices large apparatuses are needed to convert energy via the pulsatile flow of the blood by a series of coils and pulleys. With such a large structure, there come the complications of (1) size, (2) biocompatibility, (3) patient comfort, and (4) potential incompatibilities with leadless technology (due to the high magnetic field that is generated). As the size of these devices would outlast any feasibility of implantation due to the increased opportunity for a biological rejection or fibrosis cap formation which may inhibit the mechanism [5]. Also, patient comfort would also likely be decreased as the noticeable apparatus would require surgical implantation and perhaps cause irritation due to large size. Finally, the size of the mechanical device would inhibit its implantation into the ventricular cavity of the heart necessary to attach to the new leadless technology mentioned above or would require excessive surgery to maneuverer such leads through the cardiac system. Thus, a device which utilizes electromagnetic induction must account for (1) the size, (2) biocompatibility, (3) patient comfort, and (4) incompatibility with leadless technologies.

A potential solution may be with, MEMs (micro-electrical mechanical systems) offers a desirable alternative, Kotha et.al investigated the idea of using a magnetic fluid inside a mems device which would include a pump, reservoir, and electric coils inside a tubing housing [6]. In which the magnetic fluid by electromagnetic conduction would continue to be circulated to generate power. There are a few issues with such a design, namely that the pump would draw excess power away from the recharging system. By the conservation of energy, such a design to "make" energy in such a fashion of using a pump and a magnetic fluid loop is infeasible as there would be significant energy lost to the environment and being placed into the pumping motor. However, the concept of using such a magnetic fluid is of desirable trait if the problem of a natural pump could be solved.

MEM's technology also offers another alternative for energy generation due to piezoelectric materials and micro-technology machining. Inman et al. have developed a non-linear vibrational energy harvester that reacts to heartbeat waveform movement. Essentially, as the heart beats this creates a lateral deformation and this vibrational movement causes the cantilevers to bend, much akin to the shaking of keys within one's pocket during walking. Although similar to the proposed idea detailed before, this piezo-electric set up has a number of drawbacks namely it does not utilize the 3-D capabilities of piezoelectric, the pressure-induced force within the ventricular cavity, and lastly, its manufacturing procedure and insertion of the magnet components would be difficult to perform. Firstly, as Irani et al. has demonstrated in their patent is the usual piezo-electric MEM's device, as common manufacturing techniques for the micro-scale excel at 2D linear structures however, this limits the capabilities for energy harvesting by restricting the design to the two-dimensional plane. Secondly, and will be noted later in the detailed design, by being inside the ventricular cavity, an energy harvester could now utilize two sources of energy, the heart's vibrations and the turbulent flow of the blood noted by Irani et. Al. Thirdly, the manufacturing procedure to install a singular magnet tips required for the construction of such a device is unrealistic given the constraints of current MEM's fabrication technology and the size of these devices. Further there are many patents covering the field of using piezo-electric cantilevers. Because of these aforementioned issues, there is a need for a desirable product which may utilize the small size needed for leadless pacemakers, harvest the pressure-induced forces within the ventricular cavity, and be easily created.

Thus, we return to the use of electromagnetic induction, which if designed properly may use the ventricular cavity as a natural pump, i.e. solving the natural pump problem mentioned previously. Although, electromagnetic induction has been suggested to be inferior to the piezoelectric designs, [8,9] the field has significant room for improvement and provided the proper design may prove to sufficiently and creatively solve the energy dilemma faced by pacemaker manufacturers.

SUMMARY

The present invention solves one or more problems of the prior art by providing in at least one aspect systems and methods for cardiac energy harvesting of an implantable device. More specifically, the present invention includes converting previously wasted energy (via friction or pressure, for example) into power to recharge the implantable device. In this regard, aspects of the invention can include concepts of (1) electromagnetic induction, (2) blood flow in the heart, and (3) electrical recharging, and additionally use electromagnetic induction. Electromagnetic induction refers to the movement of a magnet across a magnetic coil to generate electricity.

In another aspect, a recharging device utilizing a double magnet configuration is provided. The double magnet system includes a first ring magnet interior to an induction coil and a second ring magnet surrounding the induction coil. Characteristically, the double magnet system cylindrically encloses the body of an implanted device (e.g., a leadless pacemaker), only adding millimeters to the overall height and diameter.

In another aspect, a recharging system for recharging batteries or providing power to an implantable device is provided. The recharging system includes an electric coil adapted to be coupled (e.g., inductively coupled) to the implantable device. The electric coil defines a coil interior and a coil exterior. An outer ring-shaped magnet is positioned around the coil exterior while an inner ring-shaped magnet is positioned in the coil interior. The outer ring-shaped magnet is translatable in a lengthwise direction between a first position and a second position about the electric coil and the implantable device when the recharging system is attached to the implantable device. The inner ring-shaped magnet is magnetically coupled to the outer ring-shaped magnet such that translation of the outer ring-shaped magnet induces translation of the inner ring-shaped magnet. A mechanical actuator contacts the outer ring-shaped magnet. The mechanical actuator converts compression motion into linear motion that translates the out ring-shaped magnet along the lengthwise direction. The magnet coupling to the inner ring-shaped magnet cause this magnet to also be translated. In further aspect, the mechanical actuator includes a runner supporting the outer ring-shaped magnet disposed over the coil exterior and a plurality of leaflets pivotally attached to the runner such that sideways compressive forces on the leaflets translate the runner and therefore outer ring-shaped magnet along the lengthwise direction.

In another aspect, an energy harvesting system translates the lost energy back into a cardiac implantable device (e.g., a pacemaker system) by streamlining and innovating on a traditional approach to energy harvesting, electromagnetic induction.

Some aspects of the present invention address the space constraints in the ventricles of the heart. The large setup required by electromagnetic induction has previously only served a proof-of-concept role as an intracardiac energy harvesting method. By incorporating a novel design that fits around standard pacing devices along with compliant mesh-driven ring magnets, variations of the present invention are able to utilize a classic and reliable approach to energy harvesting and apply it to cutting-edge leadless pacing technology.

In another aspect, a ferrofluid is applied with a recharging system. Ferrofluids become magnetized when localized between permanent magnets and thus act as a magnetic fluid. Such fluid would then be compressible in nature and, given a pressure, would deform or move. Thus, if an upward constricting pressure would be applied to a cylindrical container of such a fluid, the net movement of the fluid would progress upward. Then, the movement of the magnetic fluid inside of the electric coils would then begin to generate electricity, as noted by the electromagnetic induction theory in physics.

In still another aspect, an energy harvesting device configured to convert mechanical energy into electrical energy is provided. Advantageously, the electrical energy is used for charging an implantable device implanted into a patient. The energy harvesting device includes an outer sleeve composed of a soft and compressible material and an electric coil positioned within the outer sleeve. The electric coil is coupled to an electric circuit configured to store the electric energy generated in the electric coil. The implantable device is positioned centrally inside the electric coil. The implantable device is electrically coupled to the electric circuit and configured to be charged by the electric circuit. A ferrofluid partially fills the electric coil. Advantageously, the ferrofluid is configured to fluidically move within the electric coil when the outer sleeve is compressed. The energy harvesting device also includes a set of magnets coupled to both ends of the electric coil configured to apply a magnetic field to the ferrofluid to magnetize the ferrofluid, thereby forming a magnetized ferrofluid. Characteristically, wherein when the energy harvesting device is mechanically perturbed, mechanical movements transferred to the outer sleeve cause the magnetized ferrofluid to move within the electric coil, thereby generating the electric energy in the electric coil, wherein the electric energy is used to charge the implantable device.

In still another aspect, a recharging system converts the force generated by muscular contraction to deform a ferrofluid. To apply such a force, note the environment to which this device would be maintained, the heart. While oscillating between the filling and pumping stages, the heart's blood flow offers an excellent opportunity to apply the forces required by such ferrofluids. During the pumping stage of the heart, the blood within the ventricular cavity would be forced out due to the difference in pressure between the two chambers (ventricle and aorta). Uniquely the heart wrings out the blood within itself in the same motion as squeezing the water out of a wet towel, the motion that we desire to move the ferrofluid from rest up the cylindrical container. At the filling stage of the heart, the blood would pool into the ventricle chamber, decreasing the pressure onto the device and thus allowing the ferrofluid to return to a resting position. Upon generation of the electricity, the voltage would then be sent to a circuit where a large capacitor could store the energy and charge the pacemaker when needed. The device of the present invention may include a soft outer wrapping form to protect the blood from the ferrofluid yet still allow for the deformation of the fluid. Within the wrapping would be the ferrofluid, a set of electronic coils, and a set of permanent magnets.

In another aspect, an energy harvesting device is provided. The energy harvesting device includes an outer sleeve composed of a soft and compressible material and an electric coil positioned within the outer sleeve. The electric coil coupled to an electric circuit is configured to store electric energy generated in the electric coil. The energy harvesting device also includes an implantable device positioned centrally inside the electric coil. Advantageously, the implantable device is electrically coupled to the electric circuit and configured to be charged by the electric circuit. A ferrofluid partially fills the electric coil where the ferrofluid is configured to fluidically move within the electric coil when the outer sleeve is compressed. The energy harvesting device also includes a set of magnets coupled to both ends of the electric coil configured to apply a magnetic field to the ferrofluid to magnetize the ferrofluid, thereby forming a magnetized ferrofluid. Characteristically, when the energy harvesting device is mechanically perturbed, mechanical movements are transferred to the outer sleeve causing the magnetized ferrofluid to move within the electric coil, thereby generating the electric energy in the electric coil. Advantageously, the electric energy is used to charge the implantable device.

In another aspect, when the energy harvesting device is inserted into a patient's heart, rhythmic pumping of a patient's heart compresses and relaxes the outer sleeve causing the magnetized ferrofluid within the outer sleeve to move back and forth within the electric coil, thereby generating the electric energy in the electric coil.

In still another aspect, the implantable device includes a leadless pacemaker where the mechanical movements are caused by the pumping of a heart in which the energy harvesting device is inserted.

While prior inventions mainly focus on the vibrational capabilities of the heart yet, independent of any other position within the body, the present invention advantageously uses the ventricle environment to act as a unique natural pump. One of the unique and inventive technical features of the present invention is the translation of energy that is lost back into the pacemaker system by using a novel approach to energy harvesting and the use of ferrofluid within the heart. Without wishing to limit the invention to any theory or mechanism, it is believed that the technical feature of the present invention advantageously provides for using ferrofluid for generating electricity using the natural pumping mechanism of the heart. The ferrofluids, when magnetized by two permanent magnets, may act as a liquid magnet in the present invention. Thus, when squeezed by the compressive force of the heart, it will allow the movement of the ferrofluid, and then by the theory of electromagnetic induction will cause a generation of electricity. None of the presently known prior references or work has the unique, inventive technical feature of the present invention.

Some of the advantages of the present invention include (1) low cost, (2) higher recharge rate, (3) simpler design, and (4) ease of implementation for manufacturers. The device of the present invention may include a ferrofluid, coil, and a simple circuit that may be inexpensive to manufacture. In addition, the present invention may achieve a higher recharge rate in comparison to the piezoelectric or microsphere designs as the three-dimension energy harvest may use the full volume of the pacemaker to generate energy instead of being localized to one subset. Lastly, by being in a sleeve form, manufacturers would not need excessive bypass or change requirements to implement our device.

Any feature or combination of features described herein is included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a further understanding of the nature, objects, and advantages of the present disclosure, reference should be had to the following detailed description, read in conjunction with the following drawings, wherein like reference numerals denote like elements and wherein.

DETAILED DESCRIPTION

Figure 1A:
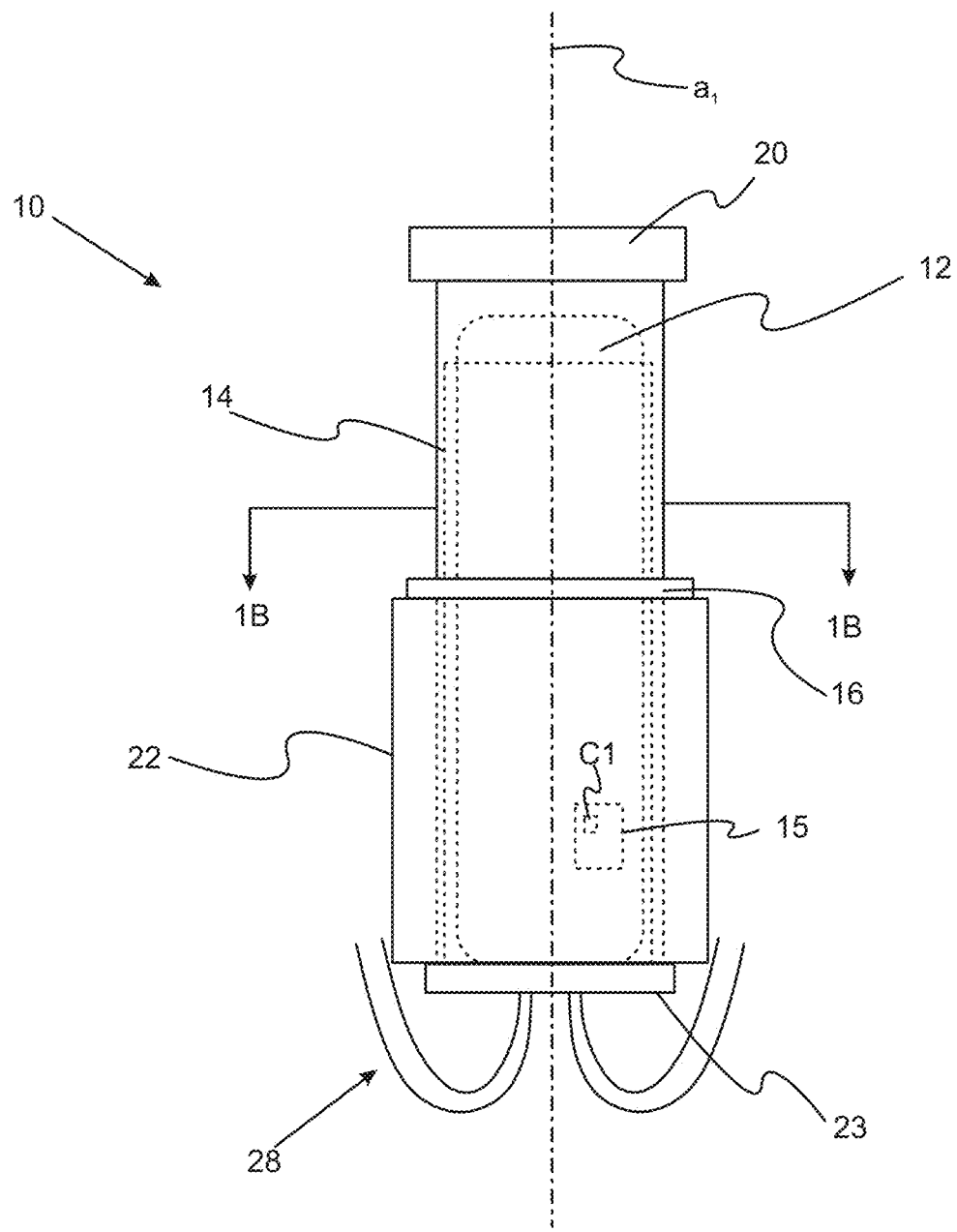
FIG. 1A. A side view of a recharging system disposed over an implanted medical device.

Reference will now be made in detail to presently preferred embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

As used herein, the term "about" refers to plus or minus 10% of the referenced number.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits.

Abbreviations

"PDMS" means polydimethylsiloxane.

"TAVR" means transcatheter aortic valve replacement.

For any device described herein, linear dimensions and angles can be constructed with plus or minus 50 percent of the values indicated rounded to or truncated to two significant figures of the value provided in the examples. In a refinement, linear dimensions and angles can be constructed with plus or minus 30 percent of the values indicated rounded to or truncated to two significant figures of the value provided in the examples. In another refinement, linear dimensions and angles can be constructed with plus or minus 10 percent of the values indicated rounded to or truncated to two significant figures of the value provided in the examples.

Throughout this application, where publications are referenced, the disclosures of these publications in their entireties are hereby incorporated by reference into this application to more fully describe the state of the art to which this invention pertains.

In general, a recharging system for recharging batteries or providing power to an implantable device is provided. The recharging system includes an electric coil adapted to be coupled to the implantable device, the electric coil defining a coil interior and a coil exterior. A magnetic component is coupled to the electric coil and adapted to at least partially surround the implantable device. A mechanical actuator is attached to the magnetic component, the mechanical actuator converting compression motion into motion of the magnetic component relative to the electric coil.

Double Ring Magnet Recharging Systems

Figure 1B:
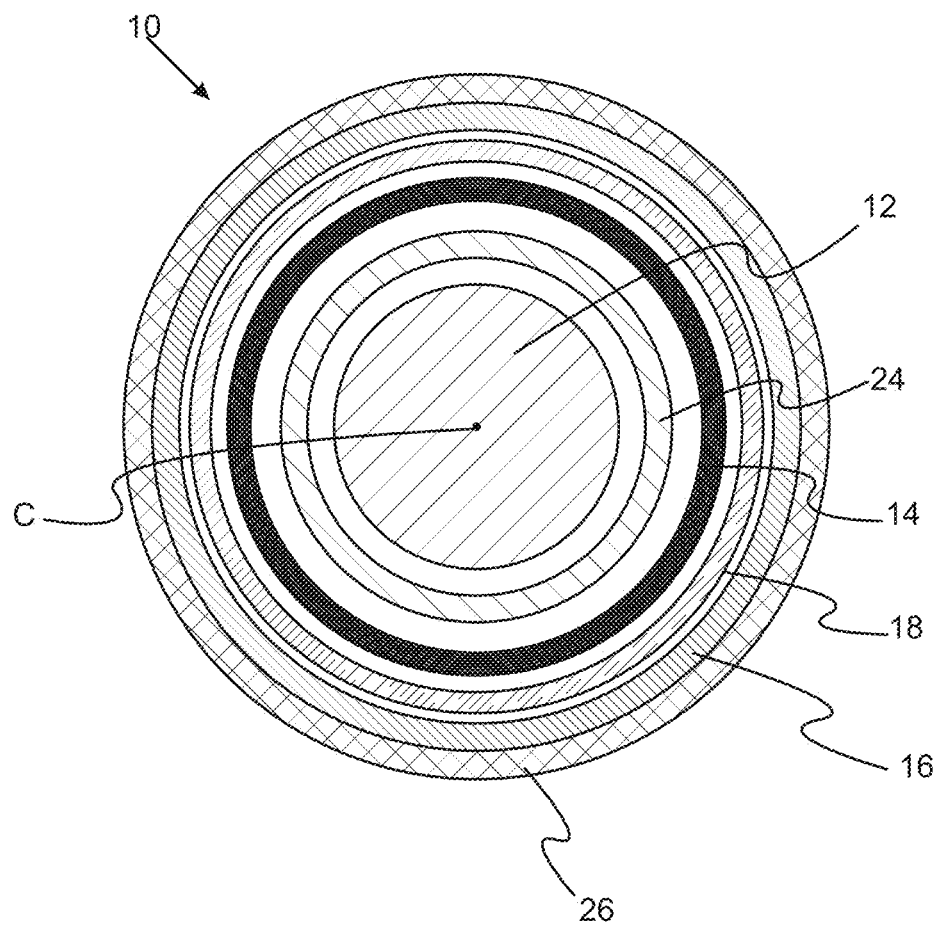
FIG. 1B. A cross-sectional view of the recharging system of FIG. 1.
Figure 1C:
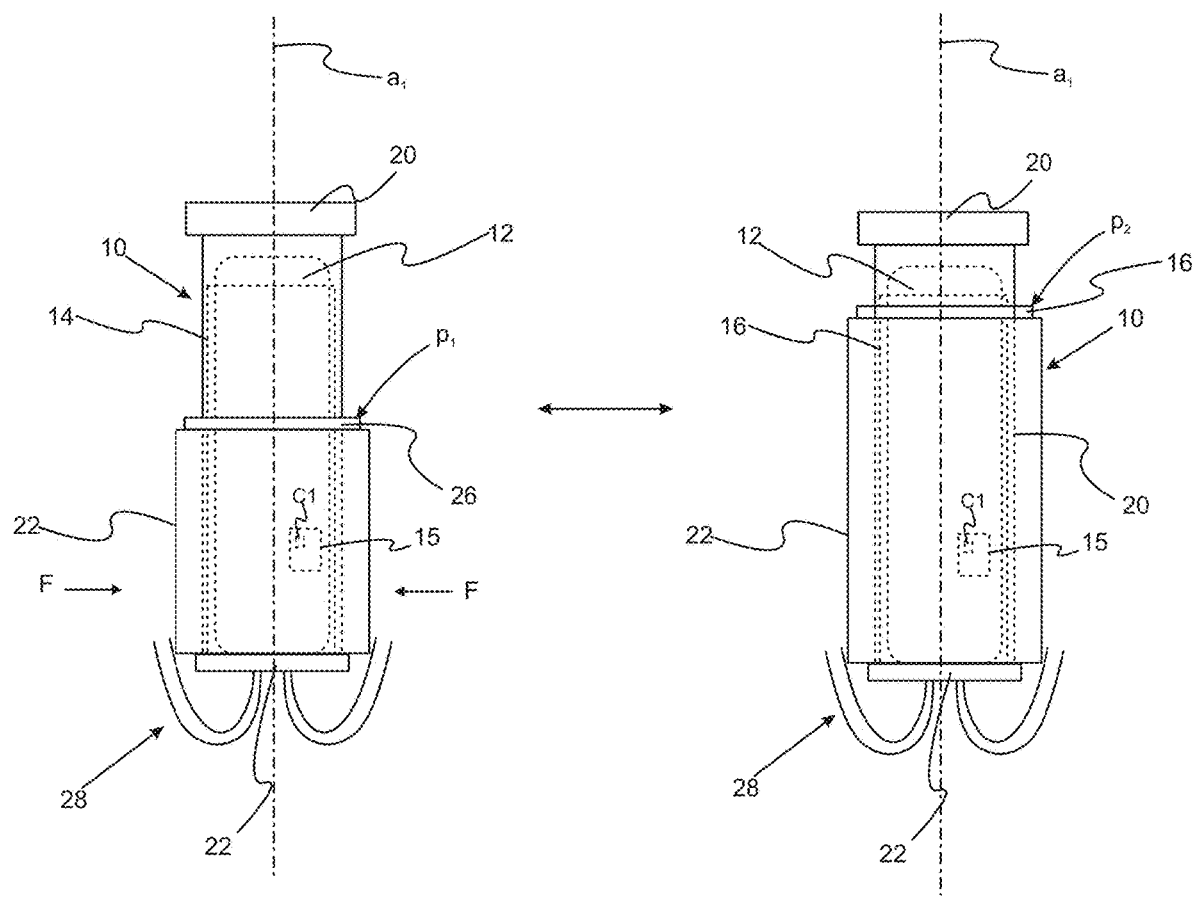
FIG. 1C. A side view of the recharging system of FIG. 1 that shows oscillation between a first position and second position induced by muscular contractions.
Figure 2A:
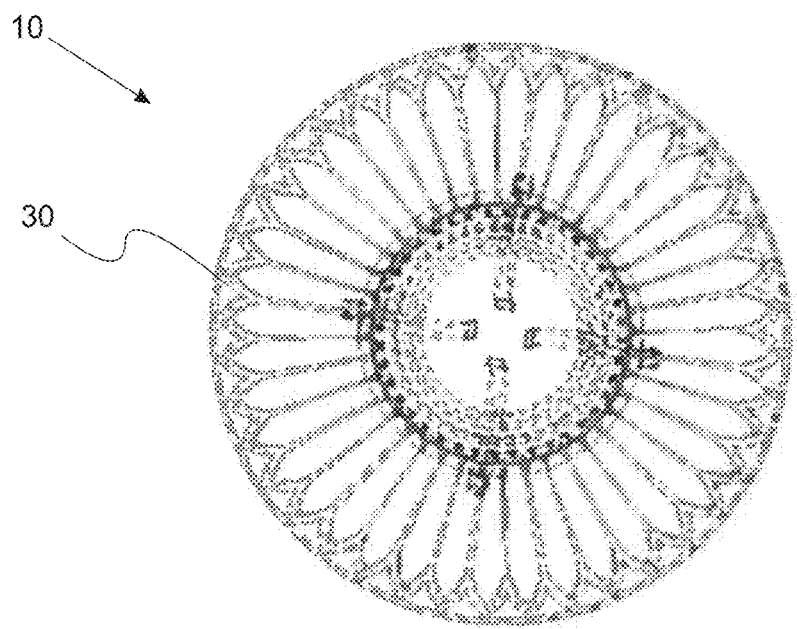
FIG. 2A. A top view of a recharging system utilizing a mesh balloon in an uncompressed state.
Figure 2B:
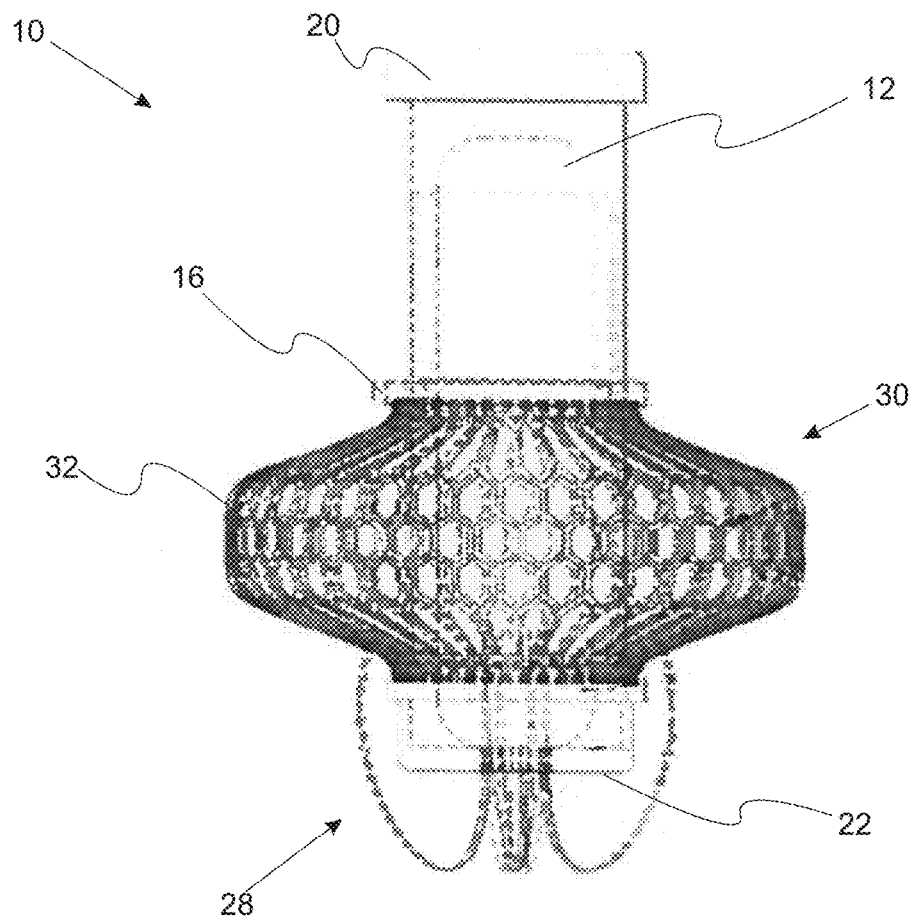
FIG. 2B. A side view of a recharging system utilizing a mesh balloon in an uncompressed state.
Figure 3A:
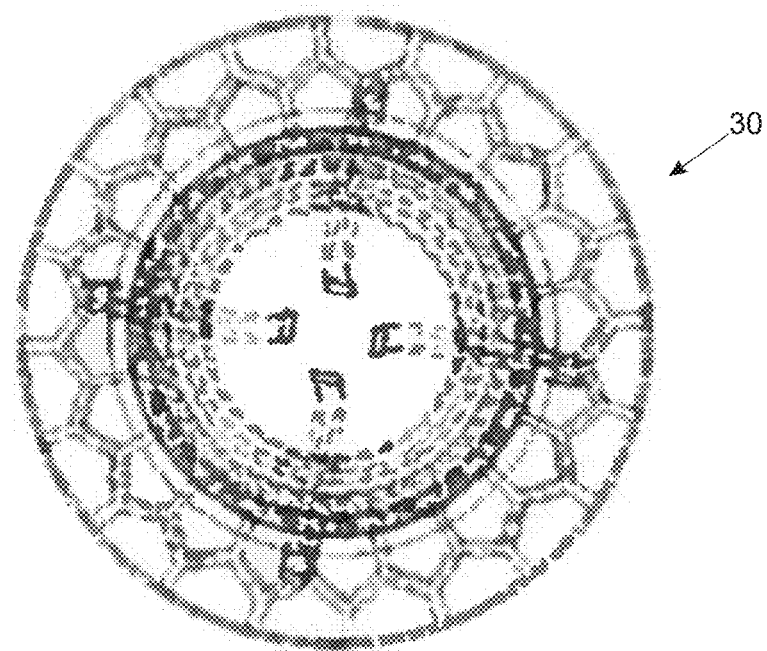
FIG. 3A. A top view of a recharging system utilizing a mesh balloon in the compressed state.
Figure 3B:
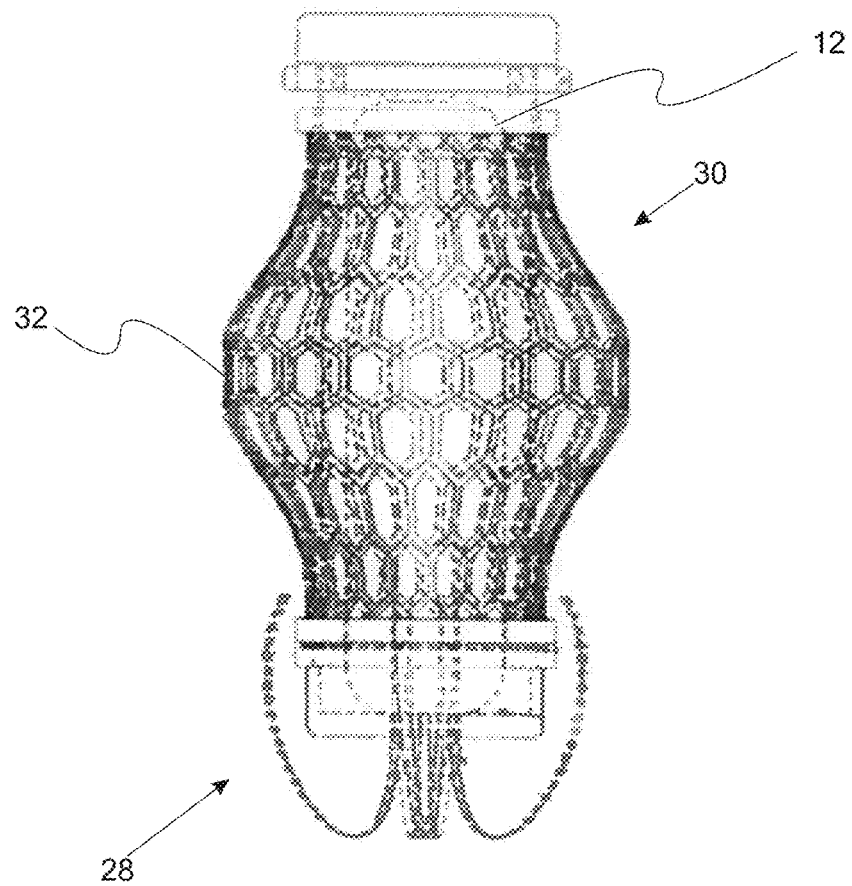
FIG. 3B. A side view of a recharging system utilizing a mesh balloon in the compressed state.
Figure 4:
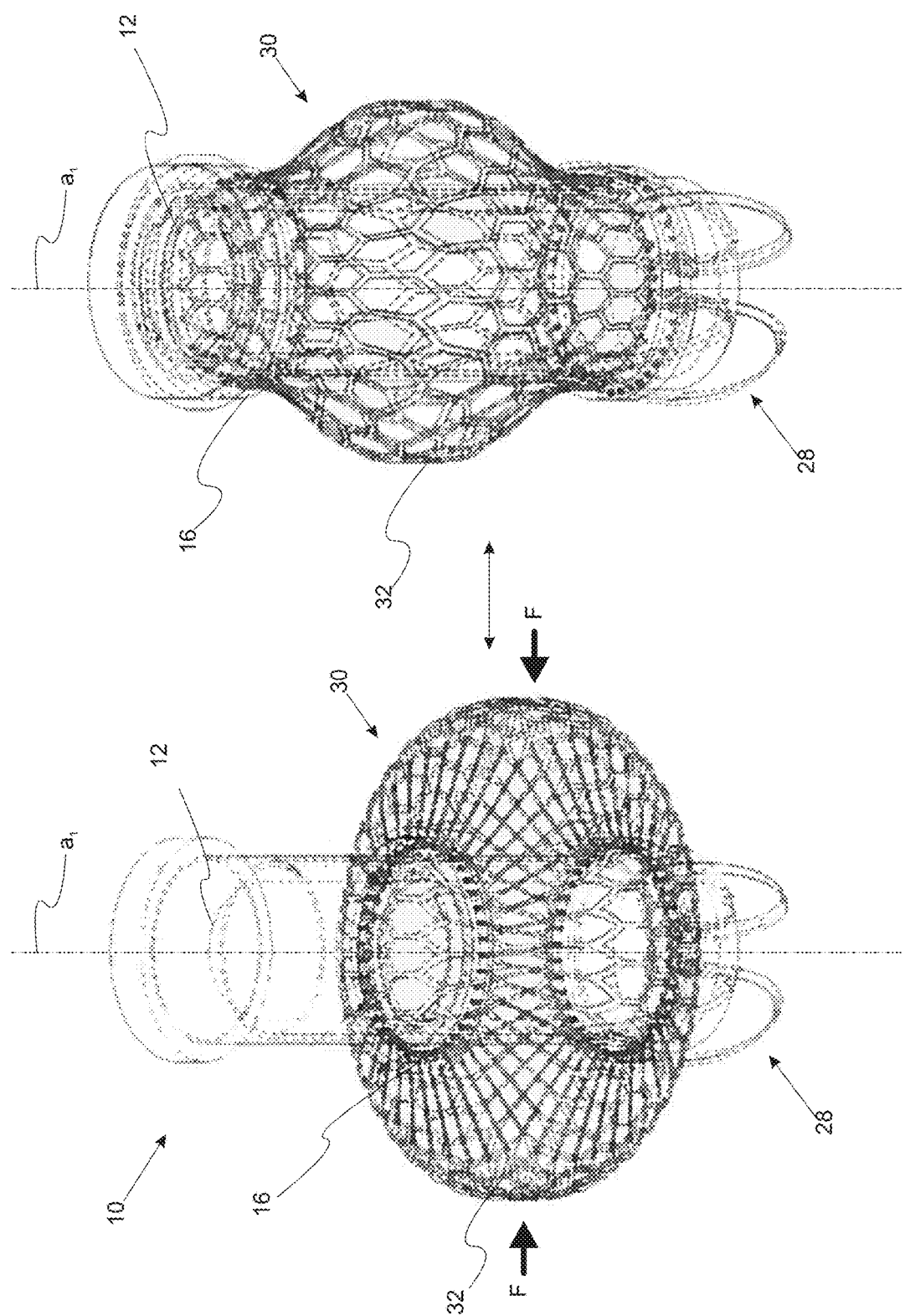
FIG. 4. A perspective view of the recharging system of FIGS. 2A, 2B, 3A, and 3B showing oscillation between a first position and second position induced by muscular contractions.
Figure 5A:
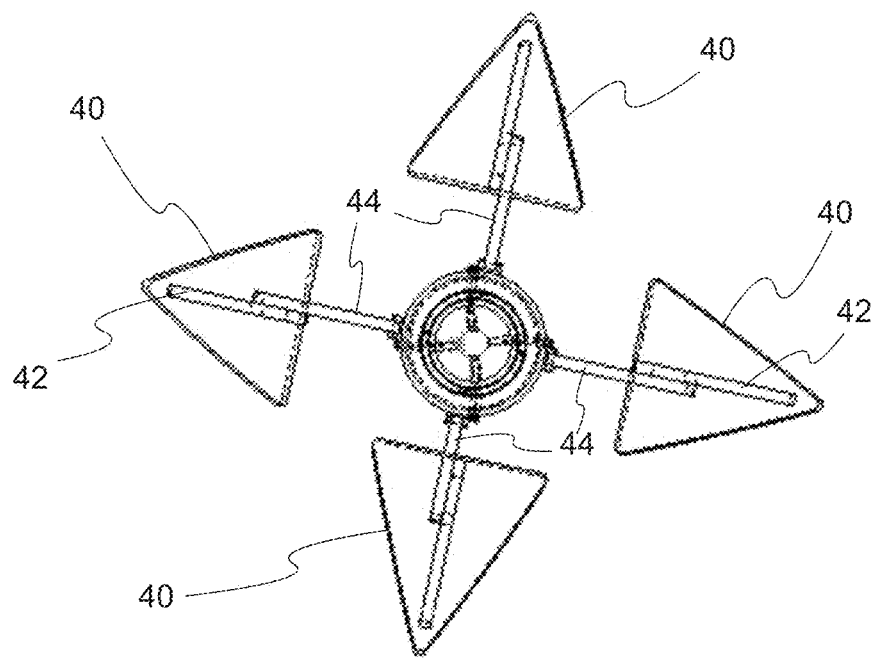
FIG. 5A. A top view of a recharging system utilizing an umbrella-like system in the uncompressed state.
Figure 5B:
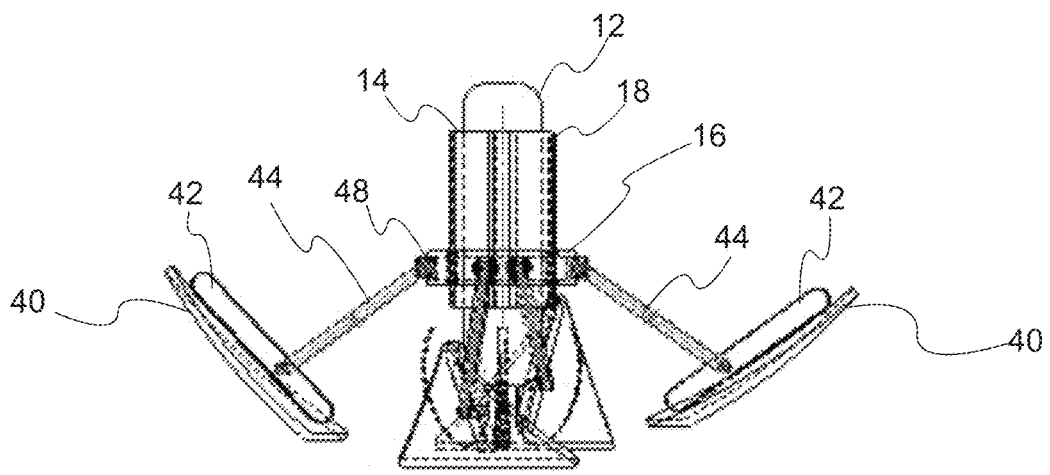
FIG. 5B. A side view of a recharging system utilizing an umbrella-like system in the uncompressed state.
Figure 5C:
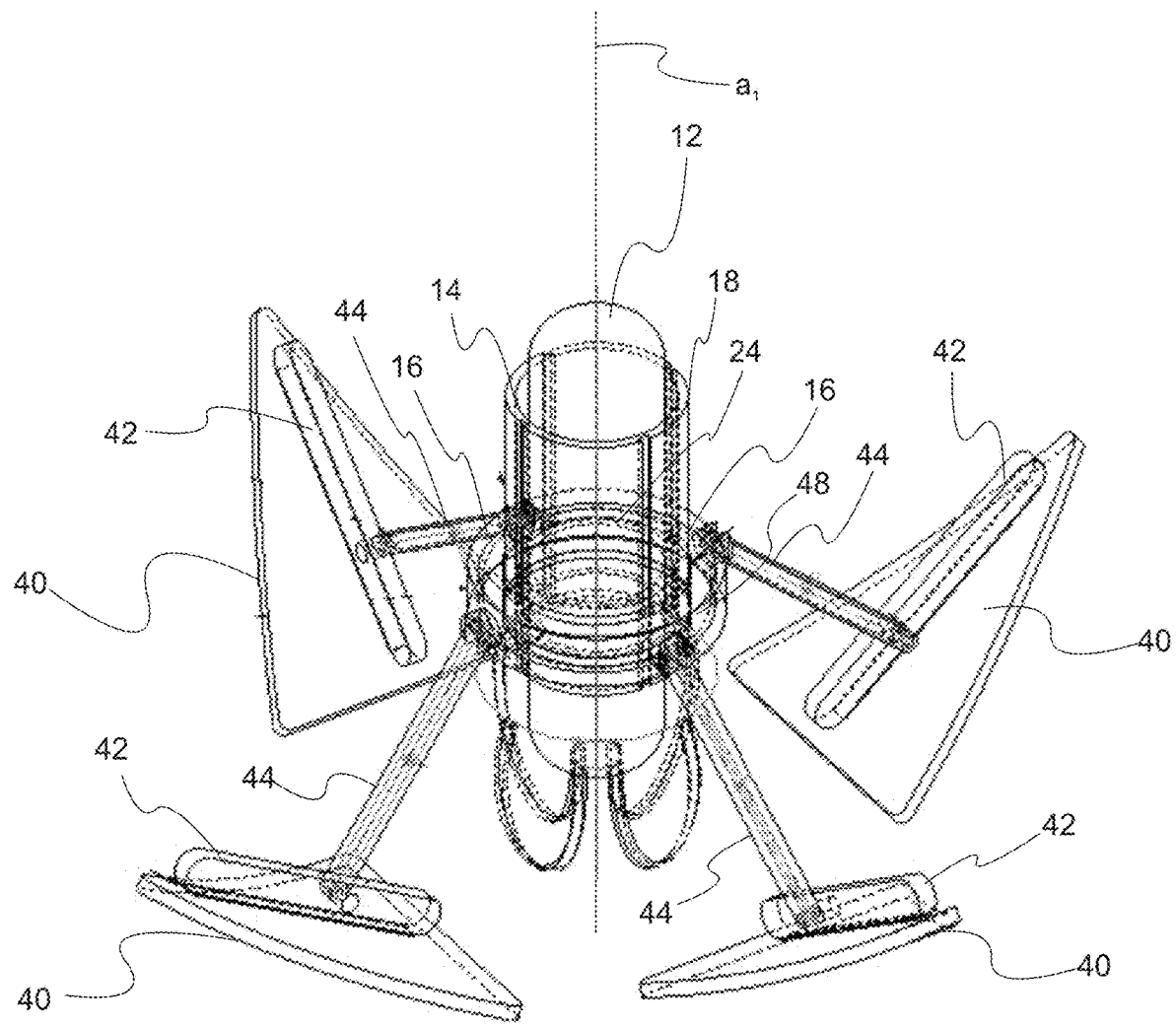
FIG. 5C. A perspective view of a recharging system utilizing an umbrella-like system in the uncompressed state.
Figure 5D:
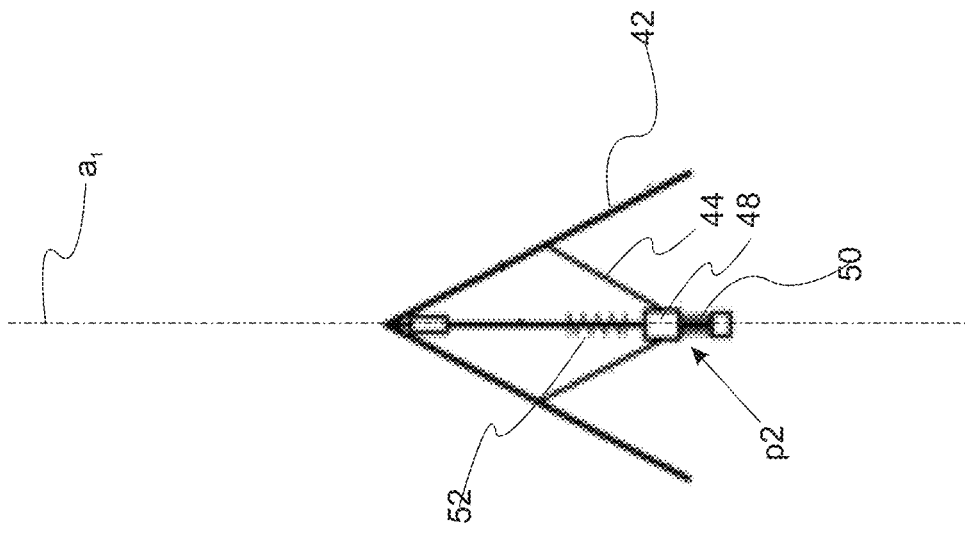
FIG. 5D. Side view of the recharging system of FIGS. 5A, 5B, and 5C showing oscillation between a first position and second position induced by muscular contractions.
Figure 5D:
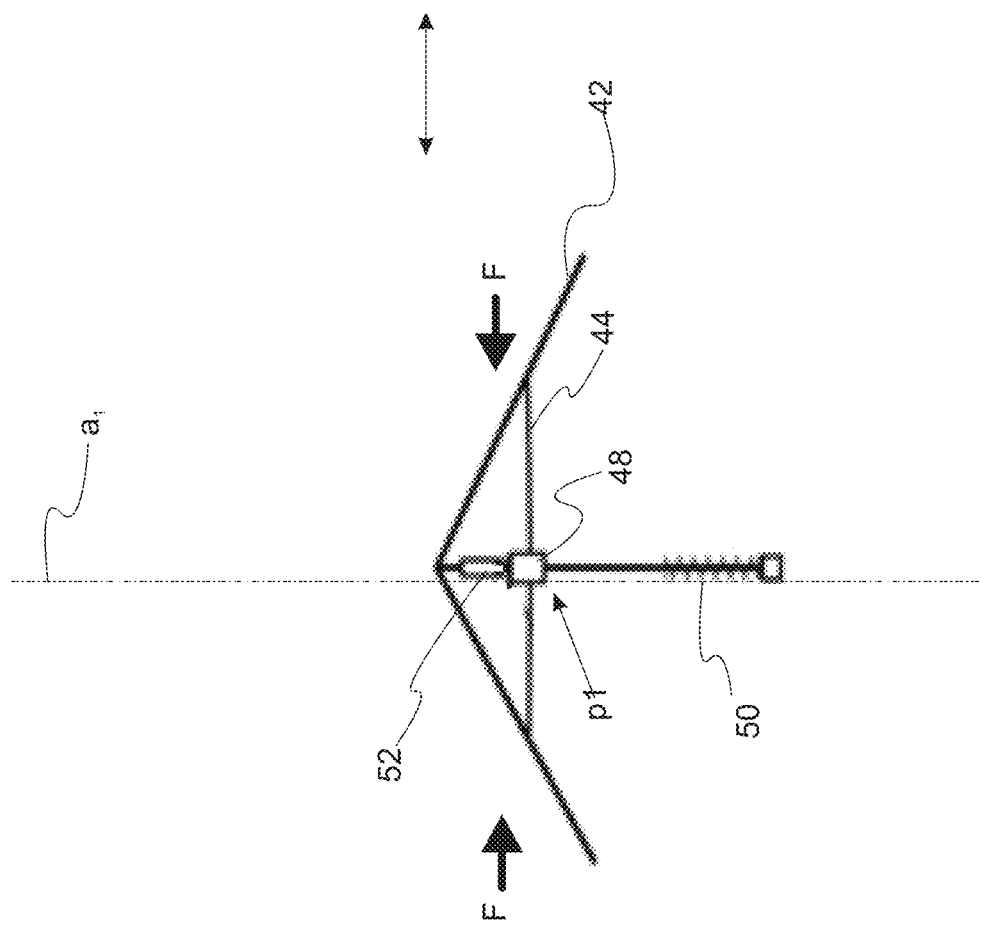

With reference to FIGS. 1A, 1B, and 1C, schematic views of a recharging system for recharging batteries or providing power to an implantable device are provided. Recharging system 10 harvests energy from muscle contractions (e.g., cardiac chambers) for this purpose. Recharging system 10 at least partially surrounds implantable device 12 to provide energy thereto to recharge a rechargeable battery. Examples of implantable device 12 include but are not limited to a pacemaker, a gastric stimulation device, a defibrillator, a neurostimulator, a diaphragm pacing device, or a cochlear implant. In a refinement, each of these implantable devices are leadless. Recharging system 10 is particularly useful for providing energy to cardiac assistive devices such as pacemakers.

Still referring to FIGS. 1A, 1B, and 1C, recharging system 10 includes electric coil 14 adapted to be electrically coupled to the implantable device 12. Electric coil 14 includes a series of wires wrapped in a tight helix to form a tube shape defining a coil interior and a coil exterior. In a refinement, electric coil 14 is (electrically) coupled to an electric circuit 15 configured to store electric energy generated in the electric coil. The electrical coupling can be a wireless electrical coupling (e.g., inductive coupling). The present variation is not particularly limited by the type and winding of the electric coil which is selected based on a desired electric energy. In a further refinement, the electric circuit 15 includes a capacitor or rechargeable battery C1 configured to store the electric energy. Outer ring-shaped magnet 16 is positioned around the coil exterior and is translatable in a lengthwise direction $a_1$ between first position $p_1$ and second position $p_2$ about the electric coil 14 (and therefore the implantable device 12) when the recharging system is attached to the implantable device 12. Coil sleeve 18 surrounds electric coil and is interposed between electric coil 14 and outer ring-shaped magnet 16. Coil sleeve 18 along with top cap 20 and bottom cap 22 form a housing of implantable device 12. In a refinement, coil sleeve 18, top cap 20, and bottom cap 23 are formed from a biocompatible polymer such as composed of poly-dimethyl silicone elastomer (PDMS) or poly(ether-urethanes).

In a refinement, the inner ring-shaped magnet 24 is positioned in the coil interior. Characteristically, the inner ring-shaped magnet 24 is magnetically coupled to the outer ring-shaped magnet 16 such that translation of the outer ring-shaped magnet induces translation of the inner ring-shaped magnet. In a refinement, outer ring-shaped magnet 16 and inner ring-shaped magnet 24 are neodymium magnets (e.g., N42 neodymium magnets). In particular, the outer ring-shaped magnet 16 and the inner ring-shaped magnet 24 are each independently composed of neodymium. It should be appreciated that inner ring-shaped magnet 24 being located internally to electric coil 14 produces the largest amount of induced electrical current due to the exponential increase of magnetic field strength towards the center C of inner ring-shaped magnet 24. The center C is the line segment defined by the centers of the circular cross sections of inner ring-shaped magnet 24.

The combination of inner ring-shaped magnet 24 and outer ring-shaped magnet 16 form a double ring magnet system. In order to physically move the inner ring magnets up and down inside the coil, which by being located internally to the coils produces the largest amount of electricity due to the exponential drop off of magnetism over a distance away from the center C of inner ring-shaped magnet 24, an outer ring magnet was needed to attract them into oscillatory movement. It is understood that magnets naturally have an unstable equilibrium, i.e., coaxial alignment of two ring magnets is difficult by design; thus, a TEFLON (or any lubricious material) sleeve encapsulates the inner and outer magnets such that the coefficient of friction between the two mechanisms is significantly reduced [12].

Mechanical actuation system 26 contacts and/or supports the outer ring-shaped magnet 16. Characteristically, mechanical actuation system 26 translates compression motion from the tissue onto which implantable device 12 is implanted into linear motion such that outer ring-shaped magnet 16 moves in the lengthwise direction $a_1$ between a first position $p_1$ and a second position $p_2$ about cardiac electric coil 14. In a refinement, the motion between first position $p_1$ and second position $p_2$ is oscillatory when the muscle to which implantable device 12 is implanted in a muscle that contracts in a periodic fashion (e.g., a heart chamber). Since inner ring-shaped magnet 24 is magnetically coupled to outer ring-shaped magnet 16, lengthwise movement of outer ring-shaped magnet 16 causes lengthwise movement of inner ring-shaped magnet 24. In a refinement, attachment tines 28 are positioned at the base of implantable device 12 to hold the device in place (e.g., in a heart chamber). In a variation, this device is aimed to be an attachment for a leadless pacemaker and will be able to be deployed in conjunction with the leadless pacemaker, which is currently deployed via an interventional catheter.

Recharging system 10 can be easily latched onto a finished implantable device 12 (e.g., pacemaker assembly) via alteration of the bottom housing of finished implantable device 12 to mate with the latching mechanism of the pacemaker. For example, epoxy resins can be used for this purpose.

With reference to FIGS. 2A, 2B, 3A, 3B, and 4, a variation of recharging system 10 in which the mechanical actuation system includes a mesh balloon is provided. In this variation, mechanical actuation system 26 includes mesh balloon 30. Mesh balloon 30 supports and/or is attached to the outer ring-shaped magnet 16. Sometimes herein, a mesh balloon is simply referred to as a mesh or a stent. In a refinement, mesh balloon 30 is made of nitinol (i.e., a nickel-titanium alloy) which is a flexible shape-memory alloy that is known for its biocompatible properties and durability. Nitinol is particularly useful because of its high structural strength and its elasticity given the repeated oscillatory movements it will be subjected to inside the ventricles. The utility of nitinol is well documented in transcatheter aortic valve replacement (TAVR) designs and is an accepted FDA material [10]. In some refinement, unique mesh patterns were implemented by various cuts/struts to increases both elasticity and elongation of the magnet pairs. These mesh patterns included differing size struts, from triangles to diamonds, to serpentine cuts. In one refinement discovered via FEA [11], diamond cuts are found to provide the greatest structural rigidity between any other design and thus with the target of reaching near 10 years or about cycles. In another refinement, a serpentine cut which increases the elongation factor of the stent design.

In a refinement, mesh balloon 30 is a tube-shaped structure typically with a central bulging central region 32 that bulges outwardly from a centerline defined by the mesh balloon. When the mesh balloon 30 is not under a compressive force F, the side bulge outwardly to a greater extent than they do when under the compressive force F. Therefore, mesh balloon 30 converts sideways compression (e.g., from the chambers of the heart) into the lengthwise translation of outer ring-shaped magnet 16 along direction $a_1$. For example, as the heart contracts, the mesh will elongate, causing the magnet attached to it to move lengthwise on the device. As set forth above, outer ring-shaped magnet 16 will move the smaller inner ring-shaped magnet 24 on the inside of the coil sleeve and inductor coil wires. Advantageously electric coil 14 generates a voltage useful for recharging the implantable device when the inner ring-shaped magnet 24 moves through the coil and/or the outer ring-shaped magnet 16 moves over the coil. In a refinement, mesh balloon is composed of a flexible shape-memory alloy. For example, a mesh-stent, made of nitinol (i.e., a shape memory and superelastic nickel-titanium alloy) translates the torquing mechanical movements of the inner heart walls into linear movement of the concentric magnet system.

With reference to FIGS. 5A, 5B, 5C, and 5D, a variation of recharging system 10 in which the mechanical actuation system 26 includes an umbrella-like runner system is provided. In this variation, the mechanical actuation system 26 includes a plurality of umbrella leaflets 40. The umbrella leaflets are mounted on ribs 42 which are pivotally attached to wire struts 44 (e.g., nitinol wire struts). In this context, "umbrella leaflets" are blades having a thickness in one refinement of 10 time less than their length and width. Typically, the umbrella leaflets are made from a soft polymer such as PDMS and polyurethanes. Wire struts 44 are in turn pivotally attached to runner 48. Runner 48 is tubular and surrounds coil sleeve 18. Moreover, runner 48 is translatable along axis $a_1$. Typically, the umbrella leaflets translate the torquing mechanical movements of the inner heart walls into linear movement by compressing wire structs 44 (e.g., nitinol wire struts) which causes translation of runner 48 along axis $a_1$ from first position $p_1$ to second position $p_2$ with respect to outer ring-shaped magnet 16. In a refinement, biasing spring 50 urges runner 48 to position $p_1$ while biasing spring 52 urges runner 48 to position $p_2$.

The sideways compression force uses the pivot connection of the leaflets 40 and the struts 44 to convert it into linear motion to move the double ring magnet system to induce an electromagnetic current as set forth above with respect to FIGS. 1A, 1B, and 1C. This system mimics the arms of an umbrella that are propelled outward through a vertical motion. In a refinement, nitinol is used for the construction of the ribs and struct because of its high structural strength and its elasticity given the repeated oscillatory movements it will be subjected to inside the ventricles. The utility of nitinol is well documented, for instance, in transcatheter aortic valve replacement (TAVR) designs and is an accepted FDA material [10]. The outer ring magnet 16, attached to and linearly driven by the runner system, attracts the inner ring-shaped magnet 24 to oscillate back and forth inside the coil, generating electrical current via induction.

The importance of magnetic shielding within a pacemaker related device is an important consideration in the design of recharging systems 10 set forth above. The presence of magnetic fields near electronic pacing devices can be detrimental to device function. Therefore, high magnetic permeable materials can be used to shield magnetic fields from the internals of pacing devices. Magnetic permeability, defined as the magnetic flux density divided by the magnetic field intensity, is a metric that can be used to determine a material's ability to deflect magnetic field. It was found that MuMetal, a metal with a high magnetic permeability ($\mu$) of $2.5 \times 10^{-2}$ H·m$^{-1}$, was the most effective at blocking magnetic field from the pacing element, and therefore can be implemented in the recharging system and/or implanted device.

The recharging systems set forth herein utilize energy is produced by electromagnetic induction in which an electrical voltage is produced across a conductor in a changing magnetic field. Application of Faraday's Law for a circular loop of wire enclosing an inside area A and magnetic field B going through it, where both A and B are vectors, then the magnetic flux acting on the loop is given by $$\Phi_B = \int B \, dA \quad (1)$$

Area vector A has a magnitude equals to the area of the loop ($A = \pi r^2$ with r=radius of the loop) and a direction perpendicular to the loop. If the magnetic field is uniform over the entire loop, as should be the case if the north and south poles of the magnet is in line with the central axis of the loop, then the magnetic flux equation (1) is reduced to $$\Phi_B = AB \cos \theta \quad (2)$$

where B is the magnitude of the magnetic field and $\theta$ is the angle between the magnetic field and the central axis of the loop. Faraday's Law says that the electromotive force (emf), which is also the electrical potential, induced in the loop is proportional to the rate of change in the magnetic flux:

$$\varepsilon = iR = -\frac{\Delta \Phi_B}{\Delta t} \quad (3)$$

where $\varepsilon$ is the emf (in volt), i is the induced current, and R the resistance through the entire loop. When the magnet is constrained to moving along the central axis of the loop, we can substitute Eq. (2) into Eq. (3) and obtain:

$$iR = -A \cos \theta \frac{dB}{dt} \quad (4)$$

For a coil with N loops, the resulting induced voltage is:

$$iR = -A \sum_{k=1}^{N} \left( \cos \theta_k \frac{dB_k}{dt} \right) \quad (5)$$

where t is the time, $B_k$ is the magnetic field strength on loop #k and $\theta_k$ is the angle between the direction of magnetic field and loop #k. Since the motion of the magnet moving back and forth through the coil is determined by the heart rate, and thus the rate of change in B is fixed. The loop area A is constrained by the size of the coil and cannot be made bigger than necessary. Therefore, to maximize the induced voltage, the number of turns in the coil, N, should be as high as physically possible.

Ferrofluid Recharging Systems

In another variation, the magnetic component is a magnetized ferrofluid fluidly coupled to the electric coil. In a refinement, the mechanical actuator includes a compression sleeve wrapped around the electric coil and the magnetized ferrofluid such that a mechanical force applied to the compression sleeve causes movement of the magnetized ferrofluid within the electric coil as set forth below. The movement generates an electric energy that is used to charge the implantable device.

Figure 6A:
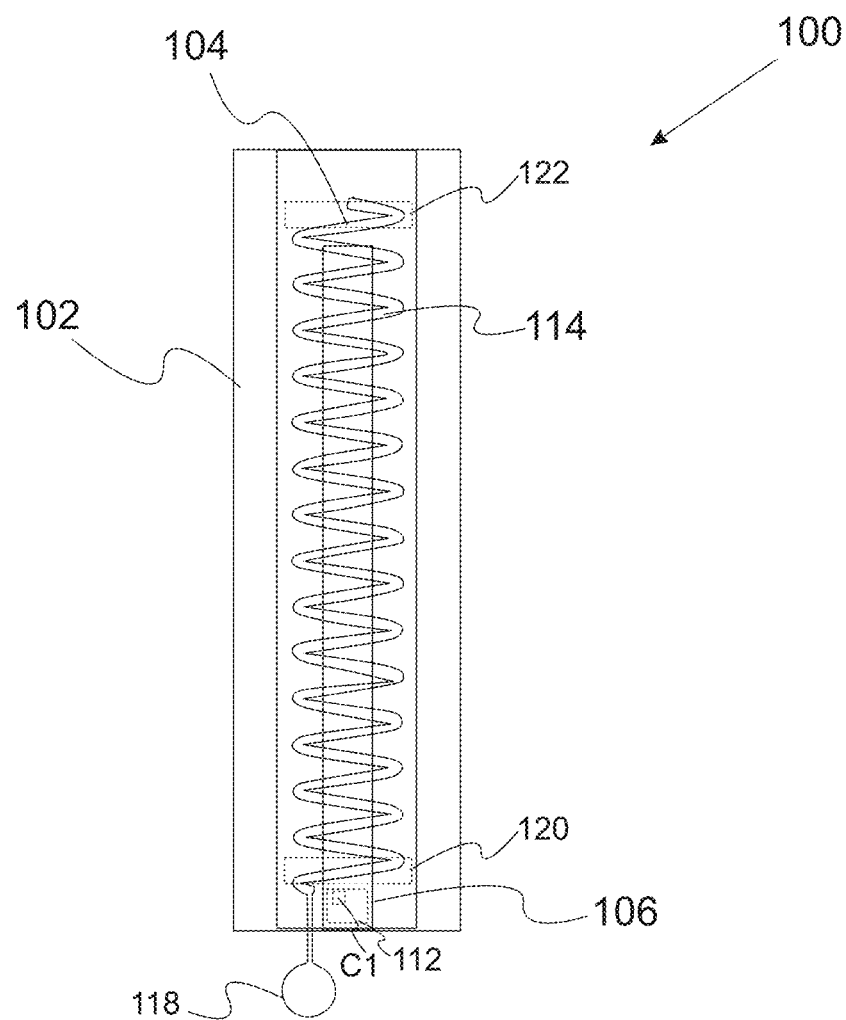
FIGS. 6A and 6B. An energy harvesting device having a ferrofluid contained within an electric coil that is configured to generate electric energy within the coil that is further used to charge an implantable device positioned within the coil, according to an embodiment of the present invention.
Figure 6B:
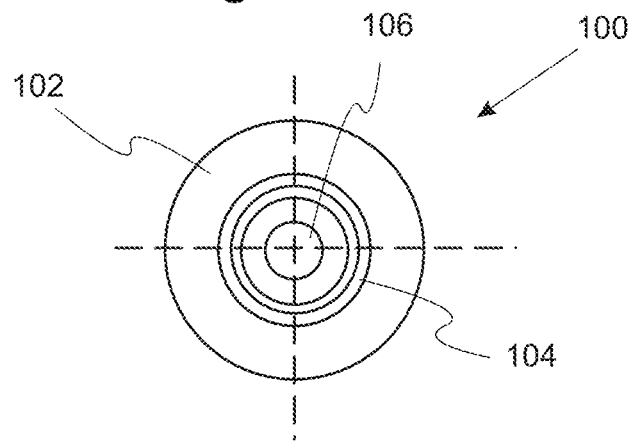

Referring now to FIGS. 6A and 6B, a variation of the recharging system that uses a ferrofluid is provided. Energy harvesting device 100 (i.e., the recharging system) includes an outer sleeve 102 composed of a soft and compressible material, and an electric coil 104 positioned within the outer sleeve 102. The outer sleeve 102 may also be referred to as a housing of the device 100. The outer sleeve 102 may be composed of a biocompatible material, which allows the device 100 to be inserted into tissues, for example. Herein, an implantable device 106 may be inserted centrally within the electric coil 104. As such, the electric coil may include an electric circuit 112 which is used to store any electric energy that is generated by the electric coil. In a refinement, electric circuit 112 can include a rechargeable battery and/or capacitor C1. In addition, the electric energy stored in the electric circuit may be used to charge the implantable device 106. As a non-limiting example, the implantable device may be a pacemaker that is implanted into a patient's heart. As such, the pacemaker may be a small device that helps the heart beat more regularly. It does this with a small electric stimulation that helps control the heartbeat. As explained previously, the main issue with the currently available pacemakers is their batters, which need frequent replacement. The present invention provides an energy harvesting tool that may be integrated with the pacemaker for charging the pacemaker using the natural pumping mechanism of the heart.

It may be appreciated that the device is not limited to a pacemaker; it may be used in conjunction with any implantable device by converting a mechanical movement into an electrical energy, as discussed below.

A ferrofluid may partially fill the electric coil (e.g., partially fill the coil interior). Originally invented by NASA as a solution to keep rocket fuel from sloshing around in propellant tanks in zero gravity, ferrofluid has since been used in the development of technologies such as higher fidelity stereo speakers and semi-active vibration dampers for mechanical and aerospace applications. Ferrofluids are defined as liquids that are strongly magnetized in the presence of a magnetic field. Moreover, a composition and a concentration of the ferrofluid is changed based on a desired electric energy. With an external magnetic field, the magnetic dipoles in ferrofluids rotate and produce a net magnetic moment, creating a parallel direction. The parallel direction of the magnetic moment creates the highest output voltage which will generate enough energy to power the pacemaker. Ferrofluids are applied to energy harvesting devices because of their magnetic properties and fluidity, making it easy for them to generate electromotive forces even with small vibrations. The ability to convert very small amounts of mechanical energy to electrical energy is the primary reason this team has chosen to pursue experimentation with ferrofluid.

The device 100 may be constructed of several different parts, which are shown in FIGS. 6A and 6B. A balloon reservoir 118 made of the same material as the housing or sleeve 102 may be coupled to the bottom of the device 100. The reservoir may be filled with ferrofluid. As such, the reservoir may be fluidically coupled to the electric coil 104 which allows the ferrofluid to move up and down the electric coil. The material of the sleeve and the balloon may be soft and compressible, as the device relies on the pressure of the heart squeezing ferrofluid through the compressible chamber. At the center of the device is a cavity for fitting the pacemaker 106 and the electronics required for recharging its battery. As shown in FIGS. 6A and 6B, the outer sleeve or housing or membrane surrounds the electric coil and pacemaker.

The device 100 may include a set of magnets 120, 122 coupled to both ends of the electric coil 104p. As such, the set of magnets may be configured to apply a magnetic field to the ferrofluid inside the device to magnetize the ferrofluid. Thus, when the device 100 is inserted into a patient's heart, rhythmic pumping of the heart may compress and relax the outer sleeve 102 causing the magnetized ferrofluid to move back and forth within the electric coil 104 (e.g., within the coil interior), thereby generating the electric energy in the electric coil 104. The set of equations that govern the generation of electric energy are shown below.

To understand the environment of the heart we turn to the literature known in the biomechanics field. Peskin, demonstrated a foundational piece of deciphering the blood flow movement within the heart and is intend for the use of this study to pose the governing equations with which we may further model the idea. Two of the necessary equations would be the Navier-Stokes Equations and the Conservation of Matter:

$$\rho(\partial_t u + u \cdot \nabla u) = -\nabla p + \eta \nabla u + F, \qquad (6.1)$$

$$\nabla \cdot u = 0 \qquad (6.2)$$

where $\rho$ is the density of blood, u is the blood flow velocity vector in 3-dimension (3D) space, $\nabla$ is the divergence, F is external force vector in 3D space, p is the pressure, and $\eta$ is the shear viscosity of blood.

It should be appreciated that, the boundary conditions include the fact that blood will not permeate through the heart ventricle (conservation of mass) and will follow the conservation of momentum by the governing fluid dynamics equation noted by Navier-Stokes as stated in Eqs. (6.1) and (6.2).

The Navier-Stokes equations are best solved with 3D finite-element analysis (FEA) with software tools like COMSOL®, which is capable of solving fluid flow coupled with mechanical pumping actions of the heart muscles.

It may be of concern by "harvesting energy," the present invention device may be robbing the body with the energy to sufficiently pump the blood. Let us then derive the expected energy to be diverted to energy generation. We begin by noting that power output of the heart may be calculated by the pressure times the flow within the heart. With an example of the average amount of blood within a human being six liter which circulates every minute, we achieve a flow of 100 cm3/s. Next, we observe the average pressure in the heart that of the 100-140 mmHg or 133,000 dynes/cm2 such that by multiplying the two (flow and pressure) we arrive at 13,300,000 ergs/s which may be converted to 1.33 watts [13]. Our device would require 30 uW of heat to be sufficient to charge the device granted even a considerable 500% inefficiency of the device system this would take, but 0.01% of the heart's energy normally used for blood transport in comparison to the 0.1 W lost to heat naturally [14]. Furthermore, if we consider that this energy (0.01%) likely is already lost to the system by the applied pressure force onto the surface of the micro-implant pacemaker. Thus, we aim to essentially convert the wasted energy into a sustainable source for implantable pacemakers. To prove these estimations, we intend to run the necessary simulations in our laboratory through the physics modeling software COMSOL®. Furthermore, contraction within the left ventricle is not unilateral, rather a twisting or wringing motion which we believe to be beneficial for our device [15]. As it will cause a greater movement of the ferrofluid by squeezing the bottom of the device and forcing the ferrofluid up to the end of electrical coils. Visually this can be depicted using imaging techniques and computation software.

Pressures reached during a cardiac cycle have been determined. A cardiac cycle involves systole (pumping) and diastole (resting) phases. During systole, the pressure in the left ventricular cavity may be about 140 mmHg.

Thus, the blood flow pressure in the heart is sufficient to squeeze the sleeve and thus ferrofluid encased there within. Herein, the sleeve is composed of a soft and compressible material, which is also biocompatible. Many biocompatible polymers contain low stiffness and may be resilient to prolonged stress. Such a list includes but is not limited to polydimethylsiloxane (PDMS) or Poly(ether-urethanes) (PU). PDMS is noted to be one of the easiest to fabricate with and includes excellent biological inertness, while PU, offers rubber-like elasticity as a useful application to the biocompatible sleeve (12). To create the necessary form factor, PDMS molds may be created to the necessary design requirements using 3-D printers or other mold making applications.

The following examples illustrate the various embodiments of the present invention. Those skilled in the art will recognize many variations that are within the spirit of the present invention and scope of the claims.

Engineering Acceptance Criteria and Tests

To comprehensively test the finalized design the following table was created for the acceptance criteria and test description to prove the device's feasibility. By categories, we have (1) Modal Analysis (Simulation), (2) Induced Voltage (Simulation/Benchtop), (4) Heat Generation (Simulation/Benchtop), (5) Magnetic Shielding (Benchtop), (6) Mesh Compliance (Simulation). These tests are outlined below in Table 1 and serve as the basis of all the test methods to be explored in the following chapters.

TABLE 1

Lists the experiments conducted for the stent designed energy harvester for in-ventricular pacemakers.

| Test Name | Acceptance Criteria | Test Description |
| --- | --- | --- |
| Induced Voltage (Simulation) | 10 µW or greater shall be generated by test set up. | Using COMSOL, the inner/magnet set up shall be tested for optimal electrical generation using the approved dimensions and 1x scaling. |
| Thermal Analysis (Simulation) | Surface temp shall not exceed 40 Degrees Celsius | Using COMSOL, the energy harvesting mechanism shall be inspected for heat generation from the current produced during actuation. |
| Mesh Compliance (Simulation) | Mesh shall deform 10 mm given 100% of heart force | Using, COMSOL, the outer "stent" or mesh will have approximate heart force conditions applied radially along its outer edge, where the elongation of the tip of the stent shall be measured. |
| Modal Analysis of Pacemaker Design (Simulation) | 1-2 Hz shall not be found as a fundamental frequency | Using Solidworks, a modal analysis shall be conducted to analyze the fundamental frequency of using the uniquely formed "stent". |
| Induced Voltage (Benchtop) | 10 µW or greater shall be generated by test set up. | Via a linear actuator, a simple inner and outer magnet set up shall be actuated where, the inner magnet slides inside the inner diameter of the 3D printed "Coils" guided by the outer magnet, being displaced by the linear actuator. |
| Magnet Shielding (Benchtop I) | Magnetic field shall be deflected greater than or equal to 75% from original field. | A thin, 1 mm thick copper sheet, shall be inserted between the space where the Micra would be located, and the inner magnet. Both the inner and outer magnet shall be present, and the gauss shall be recorded using a gauss meter. |
| Magnet Shielding (Benchtop II) | Magnetic field shall be deflected greater than or equal to 90% from original field. | A thin, 1 mm thick copper, nickel, mu-metal sheet, shall be inserted between the space where the Micra would be located, and the inner magnet. Both the inner and outer magnet shall be present, and the gauss shall be recorded using a gauss meter. |
| Magnet- Pull force (Theoretical) | Magnets do not separate during testing with lb force 3 times the heart | Using a theoretical analysis, the momentum of travel from actuation from the heart walls to the relaxation of the pressure shall be calculated using elementary momentum equations |
| Animal "Study" (Benchtop) | All parts fit within animal components | From a harvested pig heart, the 1x, 2x scale devices shall be inserted in a cross sectionally dissected heart. |
| Thermal Analysis (Benchtop) | Surface temperature does not exceed a change of 2 C. | With the optimal PDMS thickness chosen in the above testing, the device shall again be manually actuated for 15 minutes and during which the temperature shall be recorded with and without active 6 L/min water cooling |

1.0 Magnetic Core: Simulations 1.1 Introduction to Simulation Methods 1.1.1 Purpose:

To begin the simulations, the force parameters caused by the heart wall onto the mesh or stent walls would need to be defined.

1.1.2 Acceptance Criteria:

As this is literature research would be primarily for data collection the acceptance criteria for the ventricular force would be set as a range, between 10N (the lowest feasible amount for the heart) and 1 kN a value that would exceed expectations for such a pump.

1.1.3 Overview

As the pressure, defined as force/area, is well known within the cardiovascular system (167 mmHg-170 mmHg during systole and 10-11 mmHg during diastole left ventricle it is possible to extrapolate the force provided from a surface area of the heart, near the apex where the device would be implanted. To find the apex surface area, two literature sources were examined for their surface areas during and after contraction. Then these surface areas were averaged between the two sources. Using the aggregating pressures and surface areas, force was calculated. Left ventricle systolic and diastolic force are 18.9 N and 309 N, respectively. Both values pass the acceptance criteria. To note, the team decided to focus on the left ventricle as its average pressure would greatly exceed the right and would be the best-case scenario for an implant.

1.1.4 Background:

The force was calculated from the pressure and surface area using the relationship:

$$P = FA \quad (7.1)$$

Which then may be re-arranged to:

$$F = A/P \quad (7.2)$$

Knowing that A is the surface area, P the pressure in the system, and F the cross-sectional force the ventricular force for our simulations may then be calculated.

1.1.5 Materials:

Data was research in journals found using databases such as Google Scholar, PubMed, and EBSCO Academic Search Complete.

1.1.6 Methods:

Pressure values of swine heart ventricles were extracted from five sources. They were then compiled and separated based on whether the pressure was measured in the left or the right ventricle or whether the pressure is systolic and diastolic. Whenever sources contained values for the pressure of the same categories, those data points were averaged. Data points from Source 1 were thrown out from the study because the pressures were taken after a pulmonary artery banding procedure. The total surface area of swine left ventricles were calculated by dividing the scar area by the scar area percentages of left ventricles. The calculations determined from data from two different papers were averaged to be used for force calculations based on the pressure. Only the pressures of the left ventricles were calculated because only the surface area data of the left ventricle could be found.

1.1.7 Results:

TABLE 2

Scar area and percentage and calculated total left ventricle surface area.

| Total LV surface area (m²) | Average LV Surface Area (m²): |
|---|---|
| 0.0163 | 0.0137 |
| 0.0112 | |

TABLE 3

Pressure of left and right ventricles during diastolic and systolic pressure and force of left ventricle.

| | Source 2 | Source 3 | Source 4 | Source 5 | Average (mmHg) | Average (pascal) | Force (N) | Pass/Fail |
|---|---|---|---|---|---|---|---|---|
| Left diastolic pressure (mmHg) | 11 | N/A | N/A | 10 | 10.3 | 1380 | 18.9 | Pass |
| Left ventricular peak systolic pressure | 167 | N/A | N/A | N/A | 169 | 22500 | 309 | Pass |
| Right systolic pressure (mmHg) | N/A | 30 | 27 | N/A | 28.5 | 3800 | N/A | N/A |
| Right diastolic pressure (mmHg) | N/A | N/A | 4 | N/A | 4 | 533 | N/A | N/A |
| Mean right ventricular pressure (mmHg) | 25 | N/A | N/A | N/A | 23.5 | 3130 | N/A | N/A |

1.1.8 Conclusion:

Although this is a crude measurement technique for ventricular force, due to the lack of data regarding the ventricular wall force, this rough estimate proved useful for benchtop testing/simulation studies. Finding literature on the ventricular surface area for the right ventricular was scarce and thus the ventricular wall force was not calculated. However, examining the larger left ventricular pressure system does offer the benefit of a best-case condition as this would directly translate to increases in the voltage potentially possible. Therefore, if from the data shown below, if we assume the structures are the same size, the right ventricle scales at approximately ³⁄₂₀th of the force of the left ventricle.

2.0 Induced Voltage Analysis

2.1 Purpose:

The aspect of the device being simulated is the voltage output of the moving magnet inside the coil. Voltage output indicates how much power the device can generate. Without enough generation of power, and the pacemaker cannot sustain itself. Specifically, analyzed is the number of coil turns, length, and thickness to find the optimized values as well as the feasibility of this device.

2.2 Acceptance Criteria:

The acceptance criteria for this study were set to the meeting the generation of 10 µW or 5 mV given a 500 (Ω) impedance.

2.3. Overview

The study was performed using COMSOL to model the voltage output generated from a moving magnet inside the coil. The dimensions of the device were incorporated into the study. A magnet displacement of 10 mm was found to yield the highest voltage output and a wire thickness of 30 AWG seemed to output the most voltage, with the exception of the 200 turn coil, in which the 34 AWG wire yielded the highest output. All in all, with 100 mA or more of current, the simulation suggests that the device provides enough voltage to pass the 10 µW acceptance criteria.

2.4 Background:

According to Faraday's Law, whenever there is a change in magnetic flux with respect to a coil with flowing current, voltage is generated, Faraday's Law:

$$\varepsilon = -N\Delta\phi/\Delta t \quad (8.1)$$

where ε is the voltage, N is the number of turns, B is the magnetic field, A is the area, t is time. This study targeted altering the number of coil turns, as well as the area or gauge of the wire to optimize the necessary wire type to find the optimal 10 uW production.

2.5 Materials:

COMSOL Multiphysics 5.4 including the Magnetic Fields and Moving Mesh packages were utilized.

Figure 7:
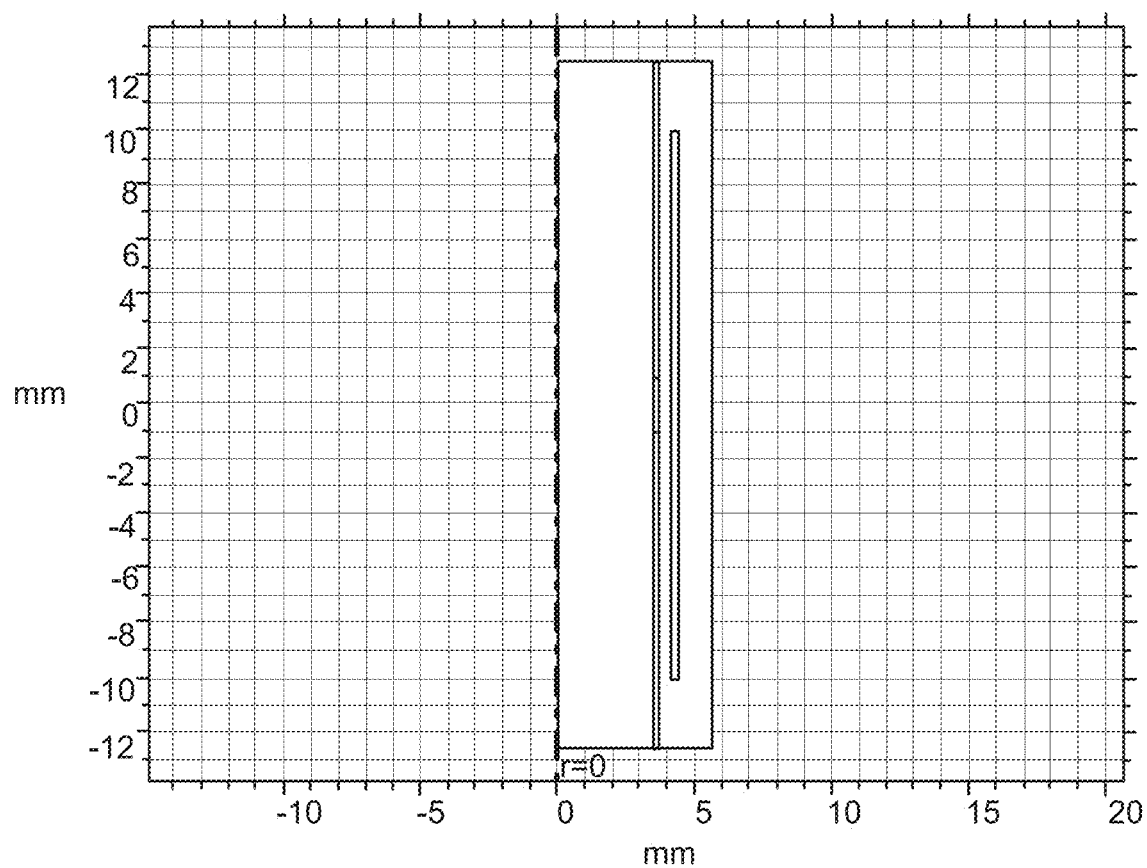
FIG. 7. Induced voltage simulation geometric set up of the device, modeled on COMSOL 5.4.

2.6 Methods:

The simulation was conducted similarly to the Induced Voltage Tutorial provided by COMSOL. The geometric modifications added were the addition of the Micra and the dimensions of the magnet and coil. (see FIG. 7) The Micra width and height are 3.5 mm and 25 mm, respectively. The magnet width and height are 0.25 mm and 2 mm, respectively. The coil width and height are 0.25 mm and 20 mm, respectively. The temperature of the system was changed from the default 293.15 K to body temperature, 310 K. The remnant flux density was adjusted to be 1.32 T in the z-direction. The prescribed mesh displacement (in the z-direction) was changed to 10 mm. The coil turns were tested with 100, 200, and 300 turns and the coil width was tested with 24, 30, and 34 AWG. Lastly, the simulation was run with 10 mA of current with a 200 turn and 24 AWG coil.

2.7 Results:

Theoretically, the displacement of the magnet should be 9 mm as the magnet is 2 mm and coil is 20 mm and they are both centered at 0 mm. However, after testing with different values ranging from 8 mm to 11 mm displacement, 10 mm displacement was empirically found to generate the most voltage.

Figure 8:
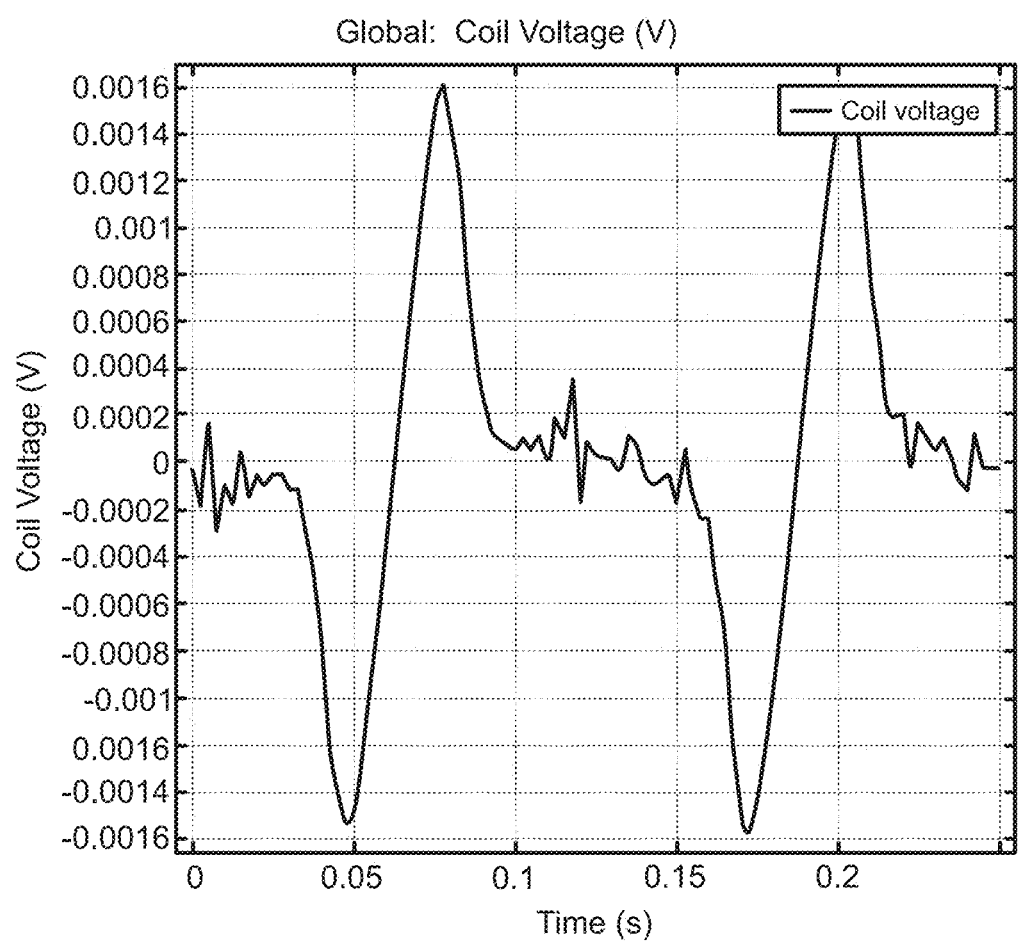
FIG. 8. Induced Voltage Simulation Results

As expected from the Faraday's Law equation, as the number of coils increased, the voltage increased as well. The 30 AWG wire yielded the highest voltage for 100 and 300 turns, 1.614 mV and 4.812 mV, respectively. The 32 AWG wire yielded the highest voltage for 200 turns of 3.227 mV. For all wire thicknesses and number of coil turns, 1 mA is insufficient current to generate 10 of power, however a 10 mA generation was more than sufficient for the task. A final test to determine the power generated from COMSOL was performed on a 200 turn and 24 AWG coil using 10 mA of current. The power generated was 30.45 µW, passing the acceptance criteria. (see results in Tables 4-6 and FIG. 8).

TABLE 4

Induced Voltage & Power from varying current within 100, 200, 300 turn coils with 24 AWG.
24 AWG Power Output

| Turns | Voltage (mV) | Power (µW) [1 mA] | Power (µW) [10 mA] | Power (µW) [100 mA] | Power (µW) [500 mA] |
|---|---|---|---|---|---|
| 100 | 1.611 | 1.611 | N/A | 161.1 | 805.5 |
| 200 | 3.045 | 3.045 | 30.45 | 304.5 | 1522.5 |
| 300 | 4.745 | 4.745 | N/A | 474.5 | 2372.5 |
| P/F | N/A | Fail | Pass | Pass | Pass |

TABLE 5

Induced Voltage & Power from varying current within 100, 200, 300 turn coils with 30 AWG.
30 AWG Power Output

| Turns | Voltage (mV) | Power (µW) [10 mA] | Power (µW) [100 mA] | Power (µW) [500 mA] |
|---|---|---|---|---|
| 100 | 1.614 | 1.614 | 161.4 | 807 |
| 200 | 3.165 | 3.165 | 316.5 | 1582.5 |
| 300 | 4.812 | 4.812 | 481.2 | 2406 |
| P/F | N/A | Fail | Pass | Pass |

TABLE 6

Induced Voltage & Power from varying current within 100, 200, 300 turn coils with 30 AWG.
34 AWG Power Output

| Turns | Voltage (mV) | Power (µW) [10 mA] | Power (µW) [100 mA] | Power (µW) [500 mA] |
|---|---|---|---|---|
| 100 | 1.526 | 1.526 | 152.6 | 763 |
| 200 | 3.227 | 3.227 | 322.7 | 1613.5 |
| 300 | 4.563 | 4.563 | 456.3 | 2281.5 |
| P/F | N/A | Fail | Pass | Pass |

2.8 Conclusion:

As the number of turns increases, the voltage output increases as well. To meet the power acceptance criteria, a current higher than 10 mA needs to be generated. Further, a 10 mm displacement provided a sufficient pathway to the most voltage. This study has some limitations for the understanding of the power output capabilities of the rechargeable pacemaker device. Because the device design includes two magnets, an inner one and an outer one, and this study only includes the inner magnet, it is not wholly sufficient to model the real-life device. However, it does provide information about baseline voltage outputs which can be used to adjust the device.

3.0 Electromagnetic Thermal Analysis 3.1 Purpose:

FDA regulations pose a 2° C. tolerance for the increase in blood temperature due to a medical device in the body. With inefficiencies built into any system, the resultant heat must be moderated COMSOL was utilized for its thermal analysis package to determine if the device would endanger patients with the use of this energy harvesting device.

3.2 Acceptance Criteria

The acceptance criteria state that the blood surrounding the device cannot exceed 2° C. more than human blood temperature, 37° C., a 312K limit.

3.3 Overview:

A simple model of the pacemaker was made in COMSOL to simulate the temperature rise due to the moving magnet inducing a voltage in the coil after 10 hours. Moving blood was also placed around the model to simulate the moving blood in the heart that would surround the actual pacemaker. After different combinations of coil turns and casing materials, the pacemaker showed that it would not raise the blood temperature over 312K with 10 mA in the device, a current specification set by the prior study.

3.4 Background:

According to Faraday's Law, when a magnet is run through a coil, a current is induced in the coil to oppose the change in the magnetic field. When a current is induced in that coil, its temperature will rise due to the inefficiency of energy transfer. The materials of the coil sheath were chosen for their known biocompatibility and ease of manufacturability; these include Parylene C, Titanium, and 304 stainless steel.

3.5 Materials:

The program used to simulate this experiment was COMSOL 5.4 equipped with the thermal analysis kit.

3.6 Methods:

In COMSOL, a rectangle of width 3.35 mm and height 25 mm mimicked the Micra pacemaker and was defaulted to its specified outer material of titanium in a 2D axisymmetric model. Enveloping the Micra, a copper rectangle set to be the coils with variable turns and a 0.5 mm offset (rectangle width of 4.85 mm and height of 27 mm) started the protectionary coil sheath made of variable material. another titanium rectangle of width 4.85 mm and height 27 mm. "Ampere's Law" and "Coils" physics were added to the simulation allowing 100, 200, and 300 turns were specified in the number of coils. 10 mA was specified in the coil current as this was the optimal current found in the prior induced voltage study. The outer casing varied between titanium, 304 stainless steel, and perylene C. To simulate blood around the device, a temperature of 310K was set acting on the device at a frequency of 1 Hz. Finally, a mesh was created, and studies were computed to observe the way the temperature around the coil was affected. The device was observed after 10 hours, sufficient time to see if a steady-state equilibrium had been reached.

Figure 9:
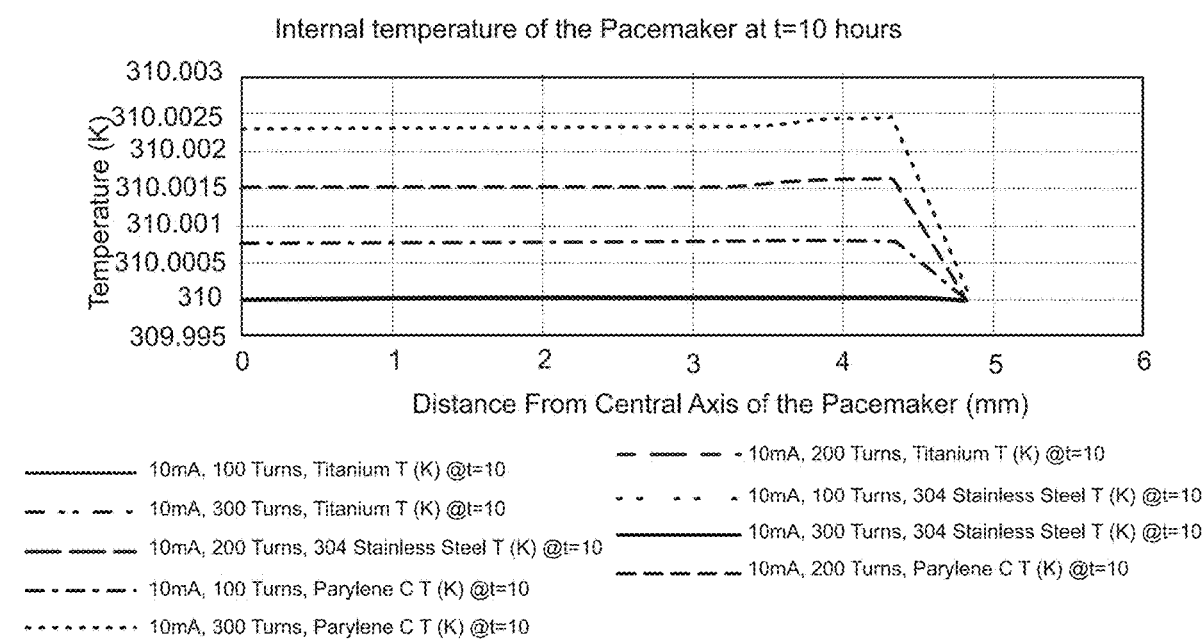
FIG. 9. Electromagnetic Thermal Analysis Simulation Results. With 10 mA running through 100, 200, and 300 coil turns and titanium, 304 stainless steel, and perylene C casings the graph shows that the temperature of each case does not exceed FDA regulation. To note, the surface of the device would be found at approximately 4.75 mm; however, with the constant cooling effect, it would never exceed the 310 limits.

3.7 Results:

All combinations of coil turns, amps, and material passed the FDA regulation, never rising above 311K displayed on FIG. 9. FIG. 9 provides electromagnetic thermal analysis simulation results. With 10 mA running through 100, 200, and 300 coil turns and titanium, 304 stainless steel, and perylene C casings the graph shows that the temperature of each case does not exceed FDA regulation. To note, the surface of the device would be found at approximately 4.75 mm however with the constant cooling effect, it would never exceed the 310 limits.

3.8 Conclusion:

All conditions passed the acceptance criteria of a <2° K increase. Further, all material choices originally listed, titanium, perylene C, and stainless steel would be considered acceptable for the design of the device.

4.0 Stent Displacement Analysis 4.1 Purpose:

The goal of this analysis is to simulate the displacement of the stents outer diameter along the central axis of the pacemaker. As noted earlier in the induced voltage simulation, the intend design of the stent consisted of a 10 mm displacement of the stent with the permanent magnet located on its distal ring. By moving 10 mm, as shown prior, COMSOL proved the capability of the system to produce 10 µW induced power enough to recharge the Micra pacemaker.

4.2 Acceptance Criteria:

The stent shall be displaced 10 mm from its original starting position given a force equivalent to that produced by the ventricular wall.

Figure 10A:
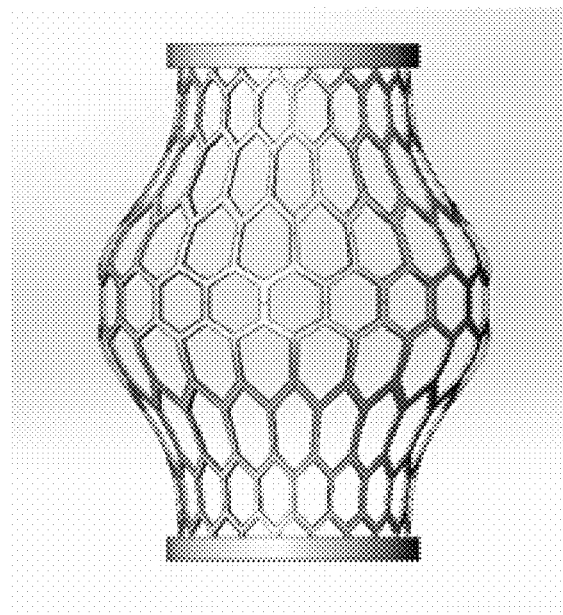
FIGS. 10A-C. Mesh Compliance Simulation set up. Where the original stent design is shown in A, in B, the stent joints proved to be too computationally complex, causing singularities to form in the simulation. Therefore, a 2D axis-symmetric analysis was run, which simplified the problem statement.
Figure 10B:
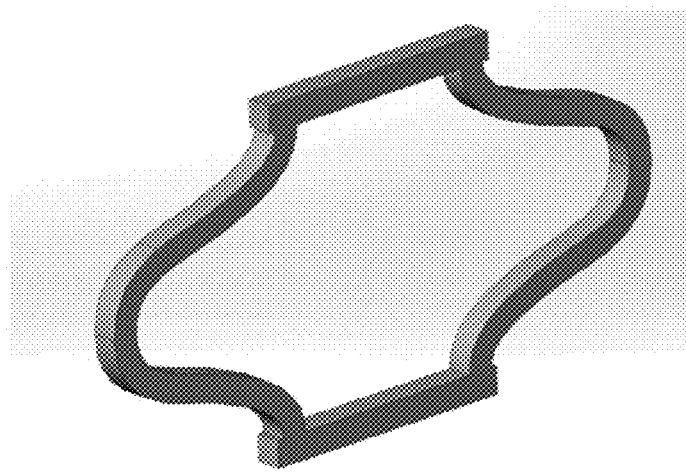
Figure 10C:
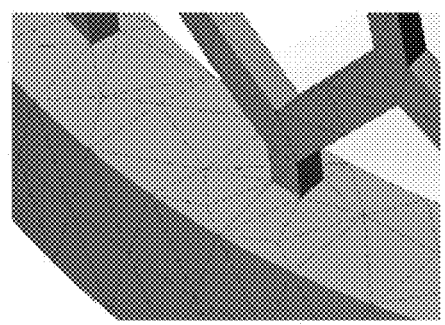

4.3 Background:

To get to the final simulations described below, the team endured multiple versions that included utilizing Solidworks for its primitive simulations package. At first, utilizing the non-linear material of Nitinol caused significant lead times for simulation completion and inaccurate results. One possible reason for the failure may have been the production of singularities at the joints of the structures. To solve this, the model geometry was greatly simplified moving from a diamond pattern to a 2D axisymmetric version. For reference, the stent in its original shape is posted in FIG. 10A and the 2D axi-symmetric version drafted for the simulation is shown in FIG. 10C. FIG. 10 provides the mesh compliance simulation set up. Where, the original stent design is shown in A, in B, the stent joints proved to be too computationally complex causing singularities to form in the simulation. Therefore, a 2D-axis symmetric analysis was run, which simplified the problem statement.

TABLE 7

Nitinol material properties assigned in COMSOL.

| Property | Value | Units |
| --- | --- | --- |
| Elastic Modulus | 83000 | N/m^2 |
| Poisson's Ratio | 0.33 | N/A |
| Shear Modulus | 10800 | N/m^2 |
| Mass Density | 6450 | kg/m^3 |
| Tensile Strength | 895 | N/m^2 |
| Yield Strength | 100 | N/m^2 |
| Thermal Conductivity | 10 | W/(m*K) |
| Specific Heat | 0.32 | J/(kg*K) |

Figure 11:
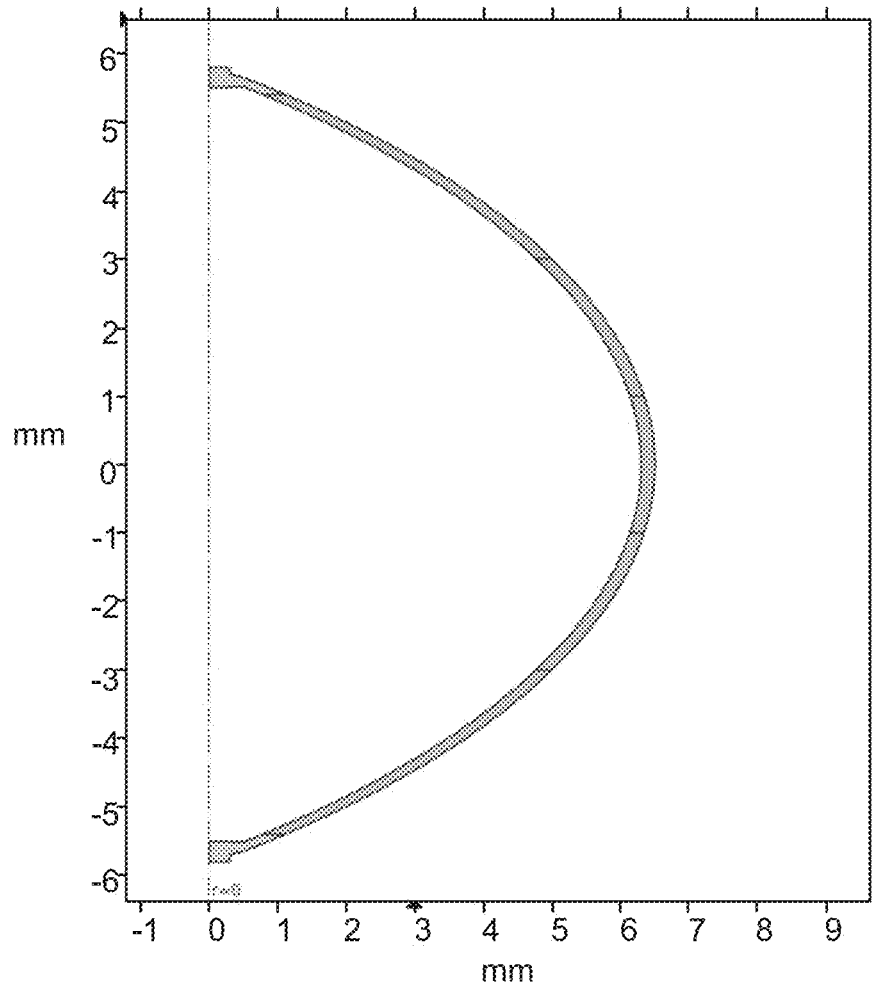
FIG. 11. The Mesh Simulation geometric set up in COMSOL.

4.4 Methods:

Within COMSOL a 5000N load on the side of the stent. A 2D-axis symmetric model was created with a split line located 3 mm from the top and bottom of the stent. This split line would act as the area in which the force could be applied upon. Fixtures for the simulation only included a fixed bottom surface at the proximal end of the stent. The total height of the stent was 12 mm with an initial width of 5 mm (chosen to fit within the normal apex of a human heart) and a thickness of 1 mm. This may be summarized in Table 8 below. Aluminum was set as the material for the ends (where the distal magnet holders would be) while the rest of the body shown in blue in FIG. 11 was set as nitinol.

TABLE 8

The Mesh Simulation key input data in COMSOL.

| Material | Fixtures | Force | Partition Area |
| --- | --- | --- | --- |
| Nitinol (Blue), Aluminum (Gray) | Fixed bottom left contacting surface | 5000N in the X direction | Middle (Top +3 mm, Bottom −3 mm) |

Figure 12A:
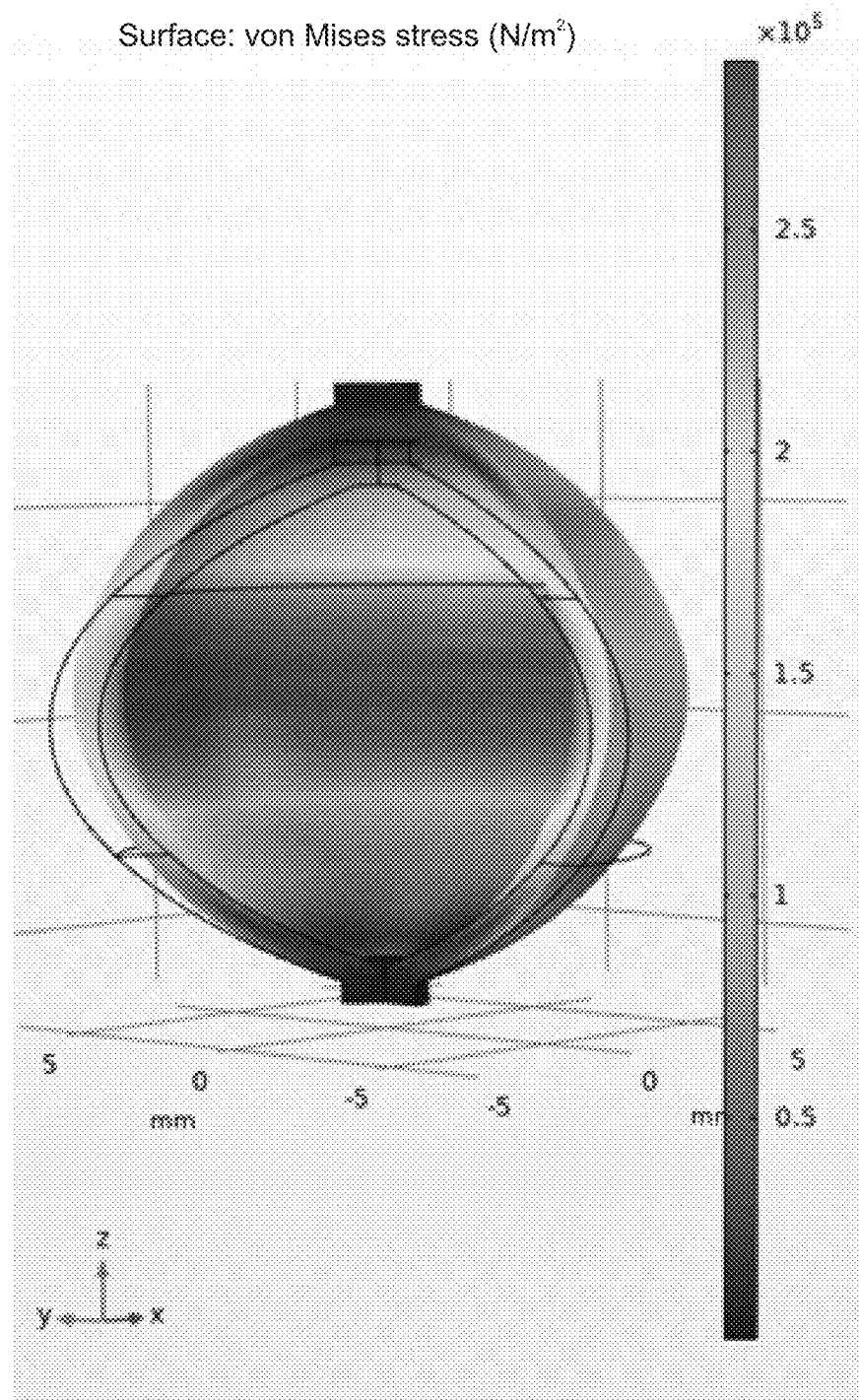
FIGS. 12A-B. The Mesh Simulation geometric results COMSOL. In A, a 5000N load was applied so that a 10 mm displacement would occur. Given the minimal expected force (30N) the displacement was significantly less as seen on the right by the axis resolution.
Figure 12B:
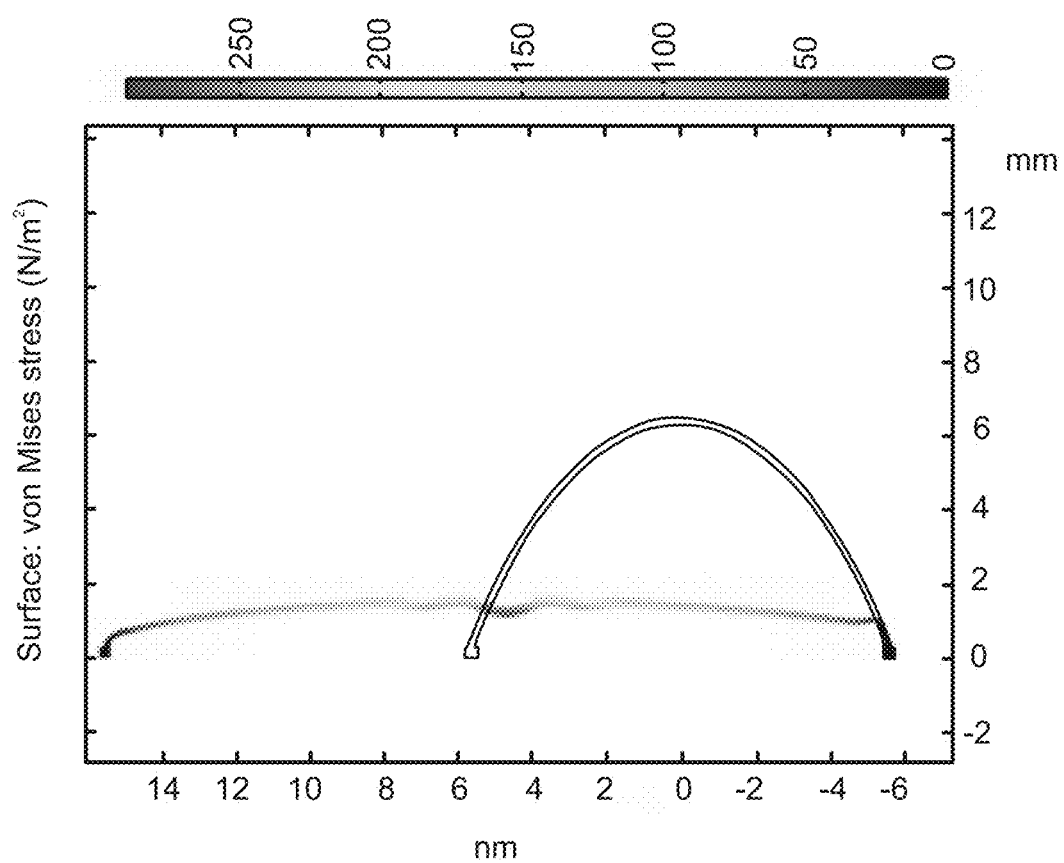

4.5 Results:

After multiple iterations, it was only in the 5000N condition which was a 16× gain from the 300N prescribed in the above that a 10 mm displacement was achieved. However, this failure may due to the following (1) the 2D axis Symmetry simplification or (2) the parameters of the stent. 2D axis Symmetry, when rotated into its 3D shape that the analysis would account for fails to include the porosity of the diamond cuts that were initially intended to decrease the stiffness and increase the elongation of the stent. To visualize the simplification problem a prior iteration derived from Solidworks shows the lack of porosity. Secondly, the parameters of the stent, i.e., its thickness, height and width may also need to be adjusted in further studies to better compensate for a 10 mm displacement. FIG. 12 provides the Mesh Simulation geometric results from COMSOL. In FIG. 12A, a 5000N load was applied so that a 10 mm displacement would occur. Given the minimal expected force (30N) the displacement was significantly less as seen on the right by the axis resolution.

5.0 Modal Analysis
5.1 Purpose:

Using Solidworks, a modal analysis shall be conducted to analyze the fundamental frequency of using the uniquely formed "stent." Importantly, if a fundamental frequency is found at the 1-2 Hz range, the device shall likely to cause it to vibrate to a point where it would break during prolonged use.

5.2 Acceptance Criteria:

1-2 Hz shall not be found as a fundamental frequency.

5.3 Overview:

A modal analysis was conducted via Solidworks frequency analysis software within its Simulation package. Upon inspection of the outer stent, the first five modes found to be fundamental frequencies were well above the operating Hz of the device thus, the device is deemed safe, from a vibrational perspective, for application.

Figure 13A:
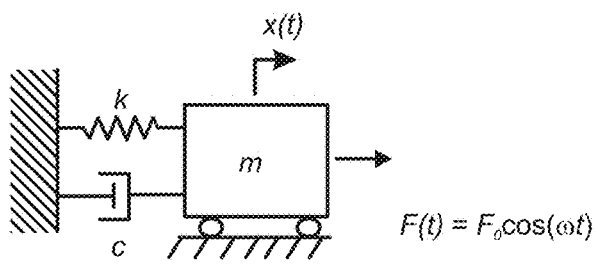
FIGS. 13A and 13B. Modal Analysis Fundamentals. In A, the mass and damper set up provides the basis for deriving the fundamental frequency. B, the heightened movement is displayed when a system reaches its harmonic or fundamental frequency in comparison to other systems, especially in underdamped systems.

5.4 Background:

The importance of finding the fundamental frequency is derived from the mathematical analysis of a spring/damper system. In it, as seen in FIG. 13A, if a mass is forced or moved, it will cause an excitation along the spring with recoil being imminent. However, by applying the correct frequency to the system a large amplitude of oscillation will be produced that may prove to be catastrophic to the system.

Figure 13B:
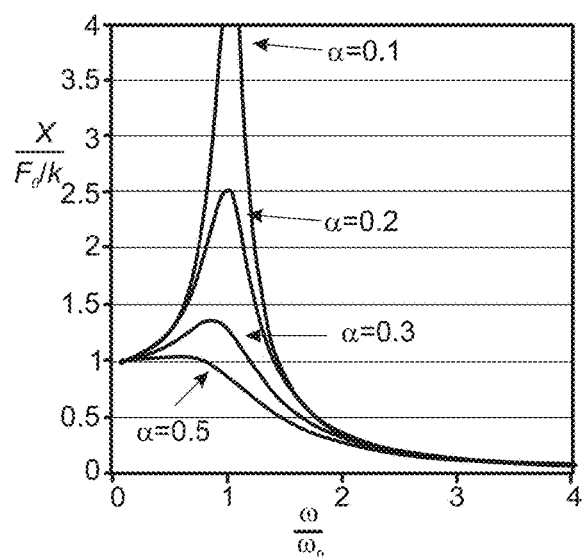

FIG. 13 illustrates Modal Analysis Fundamentals. In FIG. 13A, the mass and damper set up that provides the basis for deriving the fundamental frequency. FIG. 13B shows the heightened movement is displayed when a system reaches its harmonic or fundamental frequency in comparison to other systems especially in underdamped systems.

5.5 Materials:

Solidworks 2018-2019 for the computation software for this simulation along with the academic license to allow access to the simulation package.

Figure 14:
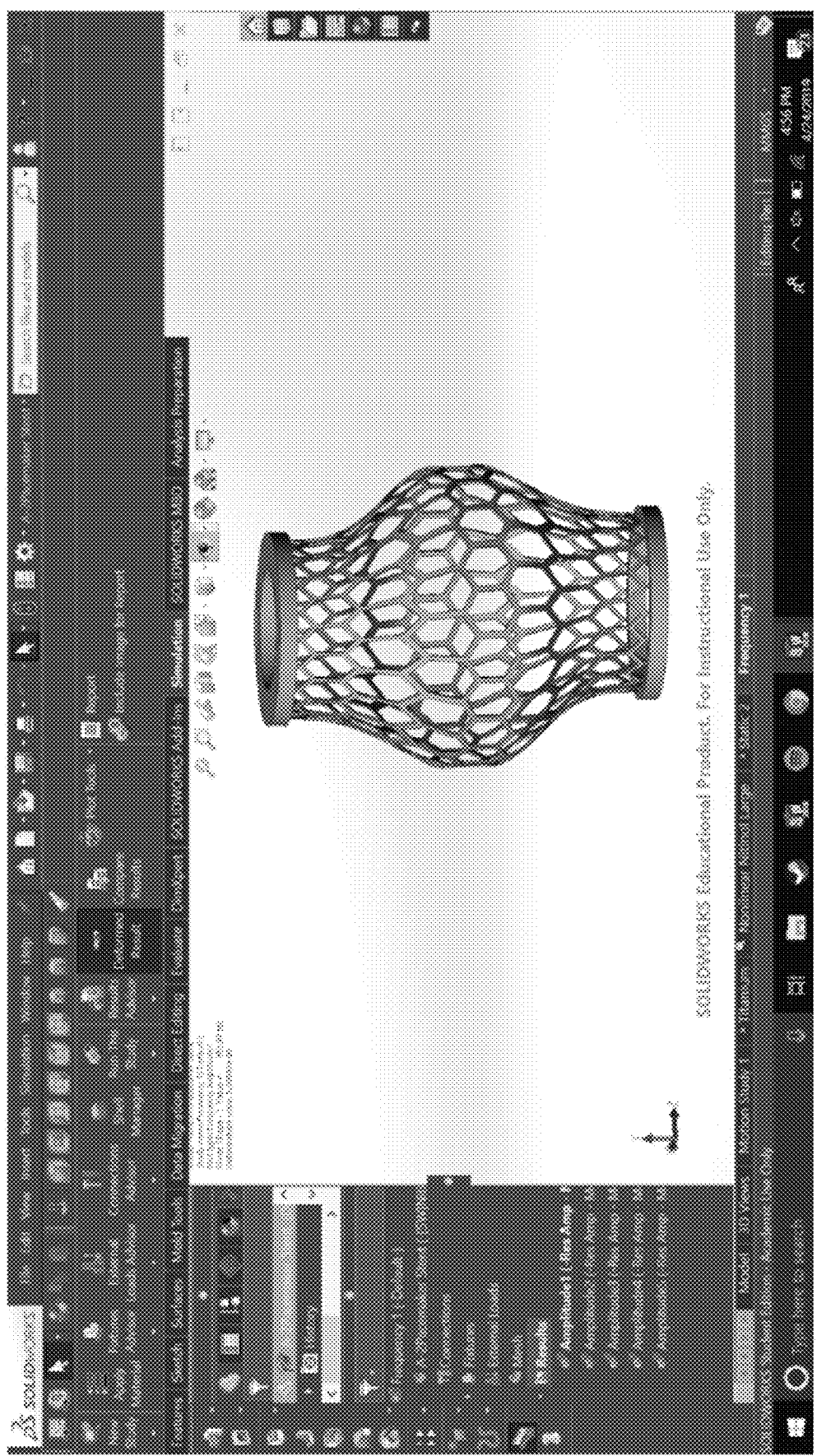
FIG. 14. Modal Analysis Stent Design Setup.

5.6 Methods:

Nitinol was applied as the material for the stent with a fixture located at the bottom face of the lower ring to mimic how the stent would be attached to the Micra. No external forces were applied as to not alter the vibration study. To visualize the test set up, a screenshot of the Solidworks stent model along with its first deformation is found FIG. 14.

5.7 Results:

No fundamental frequencies were found in the 1-2 Hz range, with the nearest resonant frequency being at 952 Hz. Thus, well above the operating conditions of the device. To support the repeatability of the simulation study, the model's details have are provided in Tables 9 and 10.

TABLE 9

The Modal Analysis Output- Fundamental Frequencies of the system.

| Mode No. | Frequency (Hertz) |
|---|---|
| 1 | 952.87 |
| 2 | 955.44 |
| 3 | 2323 |
| 4 | 6262.5 |
| 5 | 6279.2 |

TABLE 10

Modal Analysis Mesh Parameters

| Study name | Frequency 1 (-Default-) |
|---|---|
| Mesh type | Solid Mesh |
| Mesher Used | Standard mesh |
| Automatic Transition | Off |
| Include Mesh Auto Loops | Off |
| Jacobian points | 4 points |
| Element size | 0.300763 mm |
| Tolerance | 0.0150381 mm |
| Mesh quality | High |
| Total nodes | 93569 |
| Total elements | 45528 |
| Maximum Aspect Ratio | 37.3 |

5.8 Conclusion:

No fundamental frequency were found in the 1-2 Hz range and thus it meets the original acceptance criteria.

6.0 Magnetic Core: Benchtop Tests
6.1 Induced Voltage: Linear Actuator
6.2 Purpose:

With the simulated results generated from COMSOL of a 2-5 mV generation on the 1:1 scale the next item to test was the hypothesis of the utility of a double magnet (outer magnet around the electrical coils with an inner magnet) for electromagnetic generation on the large 3:1 scale. The goal of the study was twofold, (1) to test the double magnet mechanism where an outer magnet would be actuated and the inner magnet would be dragged by the outer magnets pull and (2) to test the output voltage given a 3:1 scale

6.3 Acceptance Criteria:

The acceptance criteria for this experiment is a generation of at least 10 µW of power or 5 mV.

6.4 Materials:

This setup utilizes customized 3D printed parts, our coil device, threaded rod with nut, motors, and an Arduino relay. A threaded rod and nut was used and attached to a coupler. The coupler was then attached to a 24V 3000 rpm DC motor. Customized 3D parts were made based on the dimensions of the materials used. An Arduino relay was hooked up to the linear actuator, programmed by Arduino code. The materials used for this experiment were copper wires, two magnets of different diameters, masking tape, and a 3D printed hollow cylinder. The large magnet has an outer diameter of 2 inches with and inner diameter of 1 inch. The small magnet has an outer diameter of ¾ inch and an inner diameter of ⁷⁄₁₆ inch. The hollow cylinder consists of an inner diameter of ¹³⁄₁₆ inch and an outer diameter of ¹⁵⁄₁₆ inch. This cylinder was 3D printed with the specific dimensions in order to fit both the large and small magnets. The copper coil was made from a polyurethane enameled copper wire of 34 AWG.

Figure 15A:
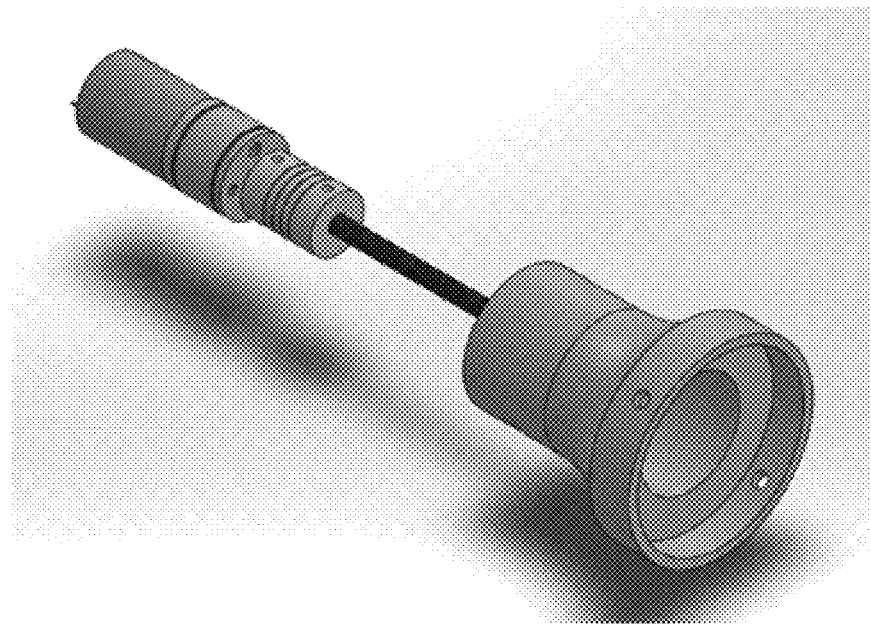
FIGS. 15A and 15B. Induced Voltage Benchtop Set up including the CAD renderings of the custom linear actuator (A) and the actual set up (B). A Custom set up was used to manipulate the outer magnet.
Figure 15B:
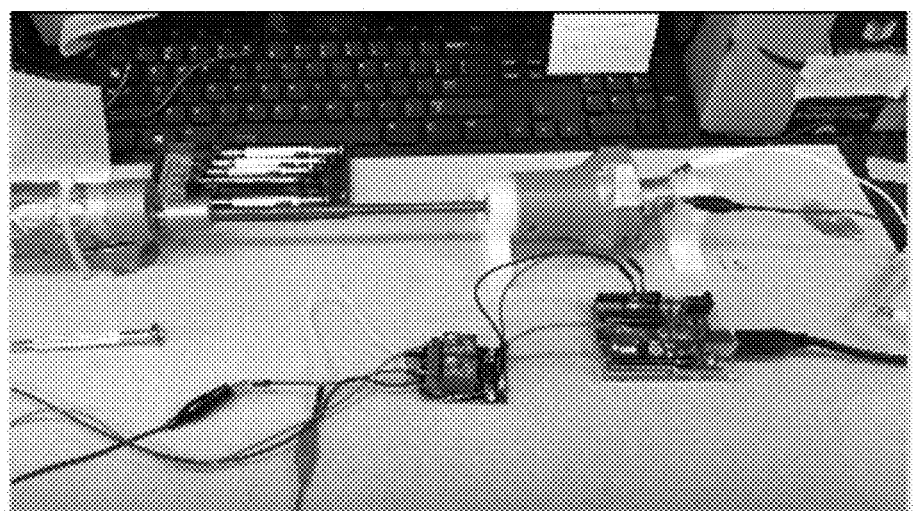

6.5 Methods:

The linear actuator was designed using rotation movement that would translate to translational movement. The nut that was fastened to the threaded rod was secured onto a customized 3D printed part which would stabilize the nut giving it a translational movement. Other customized 3D parts were used to secure the coil device to the linear actuator and was used to guide the movement of the outer magnet. The coils were held stationary on the other side and only the outer magnet interacted with the linear actuator. The Arduino relay allowed for oscillating movements, switching the direction of the linear actuator moving forward and backward to complete an approximate 30 mm path at 1-2 Hz. The linear actuator device controlled the movement of the outer ring magnet and oscillated the magnet over the coils at a constant frequency. A Solidworks rendering is provided in FIG. 15A to show the setup of the linear actuator and the final prototype used. 10 trails were completed and recorded utilizing an oscilloscope for (1) the control condition of no movement, to check for current or voltage noise and (2) the variable condition where the linear actuator would be activated.

Figure 16:
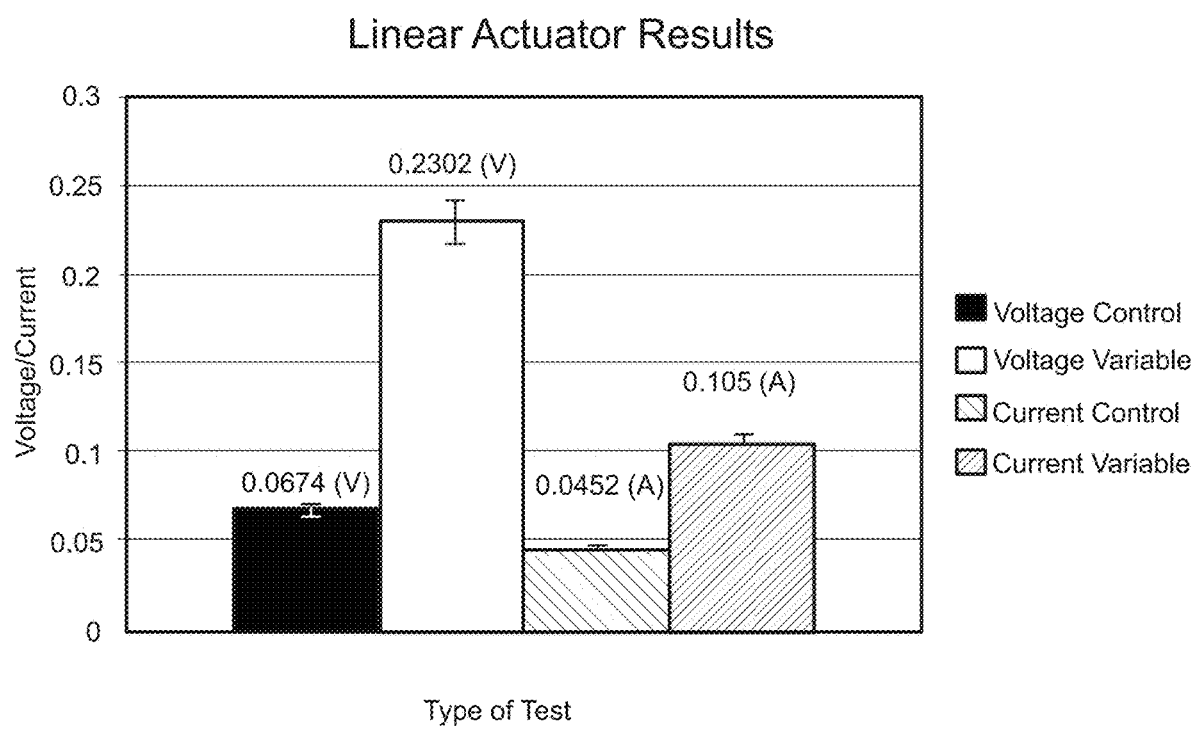
FIG. 16. Induced Voltage Benchtop Outputs. Both current and voltage are shown, where the average voltage over the 10 trials was 230 mV, far surpassing the acceptance criteria even given a 3× scaling.

6.6 Results:

FIG. 16 shows both the voltage and current during variable and control conditions. Notably, the test-set exhibited a large noise over both the current and the voltage outputs likely attributed to the small gauge wire (34 AWG) that was difficult for the oscilloscope alligator clips to attach to. Regardless, a significant increase in the variable condition was found where an average voltage of 232 mV was obtained and a current of 100 Mv.

6.7 Conclusion:

As proven from the manually actuated experiment, electromagnetic induction of two concentric magnets is functional. The linear actuator test confirmed that with a double magnet system it would be possible to harvest more than ample energy for the device. With an output of 0.2302 V, this greatly exceeds the acceptance criteria of 10 µW or 5 mV calculation even with the 3× gain factor applied to the system.

7.0 Magnetic Shielding

7.1 Purpose:

The purpose of this test was to see if copper foil was able to shield a mock pacemaker from the magnetic fields produced by surrounding magnets. This experiment is important to the team's progress on the device, as normal pacemaker function is severely affected by near external magnetic fields.

7.2 Acceptance Criteria:

The main goal of this proof experiment was to attempt to reduce the initial magnetic field read by the gaussmeter with no magnetic shielding by initially 75% and then 90% during the second test method. Given the relatively low magnetic permeability of copper ($1.26*1^{-6}$ H/m), we hypothesize that the copper shielding will aid a small amount in shielding the magnetic field from the gaussmeter.

7.2 Overview:

The ring-magnet design created to induce electromagnetism generated a magnetic field capable of interfering with the pacemaker device nested inside the magnets. To overcome this obstacle, magnetic shielding in the form of different metals coatings were investigated. Nickel foil of width 0.12 mm and a MuMetal sheet of width 0.06 mm were wrapped around a mock pacemaker and the magnetic field inside was measured with the inner and outer ring magnet setup. Nickel and MuMetal were chosen because of their relatively high magnetic permeabilities. Results showed a positive effect on magnetic shielding with the Nickel and MuMetal shielding

7.3 Background:

Magnetic shielding is a method used to redirect magnetic fields from an area of unwanted fields. The most popular materials used in magnetic shielding are called ferromagnetic materials. Alloys containing Iron, Nickel, and Cobalt also work great as shields. The magnetic permeabilities of copper, nickel, and MuMetal are $1.26*10^{-6}$, $1.26*10^{-4}$, and $2.5*10^{-2}$ respectively. The underlying hypothesis was that the effectiveness of shielding would correlate with the increase in magnetic permeability; with MuMetal being the most effective shield and Copper being the least effective shield. The thickness of shielding is also a factor in the amount of the magnetic field that makes it through the shield. It can be shown that as the thickness of the magnetic shielding increases the ability to disrupt or shield increases. The key material property magnetic permeability thus plays the largest role in determining what thickness would be sufficient to block a substantial amount of the magnetic waves.

Materials used in this test included adhesive copper foil, an F.W. Bell 5100 series Hall Effect Gauss/Tesla Meter, a ½"×¼"×⅛" N52 grade neodymium ring magnet, a ⅜"×¾"–⅛" N52 grade neodymium ring magnet, a hollow mock pacemaker and a 3D printed cylinder, with an inner diameter of ¹³⁄₁₆" and an outer diameter of ¹⁵⁄₁₆". spacer between the concentric ring magnets.

7.4 Methods:

The experimental setup was as follows: a gaussmeter was used to measure the magnetism in the setup, copper foil was wrapped around the pacemaker and the device was placed inside of 2 concentric ring magnets. The gauss values were recorded 8 times per material. A control test with no magnetic shielding was also performed. Between trials, the gaussmeter was calibrated and zeroed. Lab stands and tri-grips were used to stabilize the gaussmeter and the magnet setup. This was to avoid wildly fluctuating values that were read by holding the probe by hand pre-testing. The distance the probe was inserted into the mock device was kept constant through measuring the distance before each test.

Figure 17A:
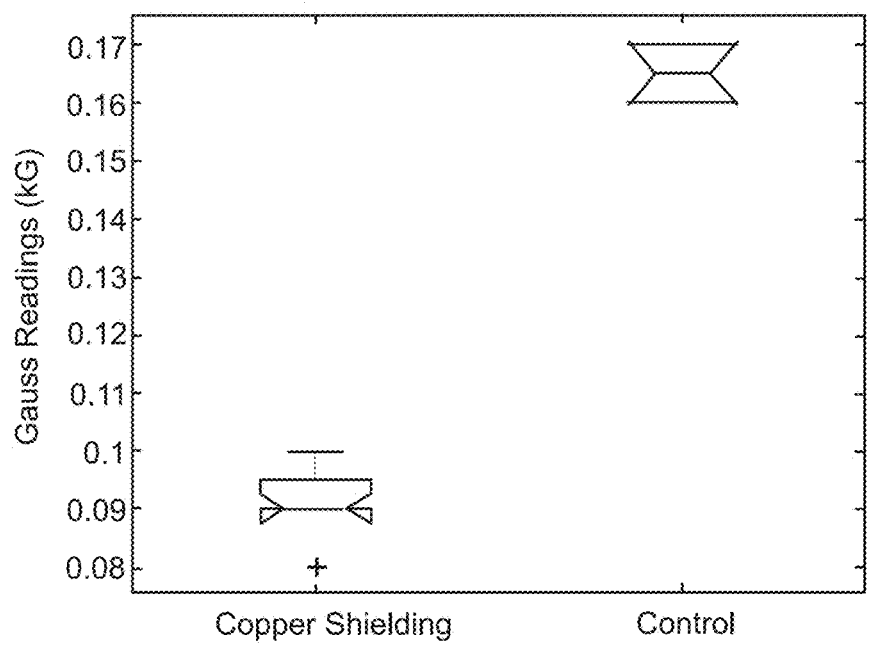
FIGS. 17A-B. Magnetic Shielding Results. Here the additional material significantly decreased the magnetic field expressed in the center of the coils i.e., where the Micra pacemaker would sit. Here the results are split, Copper/MuMetal/Nickel as the copper test was run first with a preliminary acceptance criterion of 75% reduction in magnetic field and then later the test was retried with stricter standards of a 90% reduction FIG. 18. Animal study result pictures.
Figure 17B:
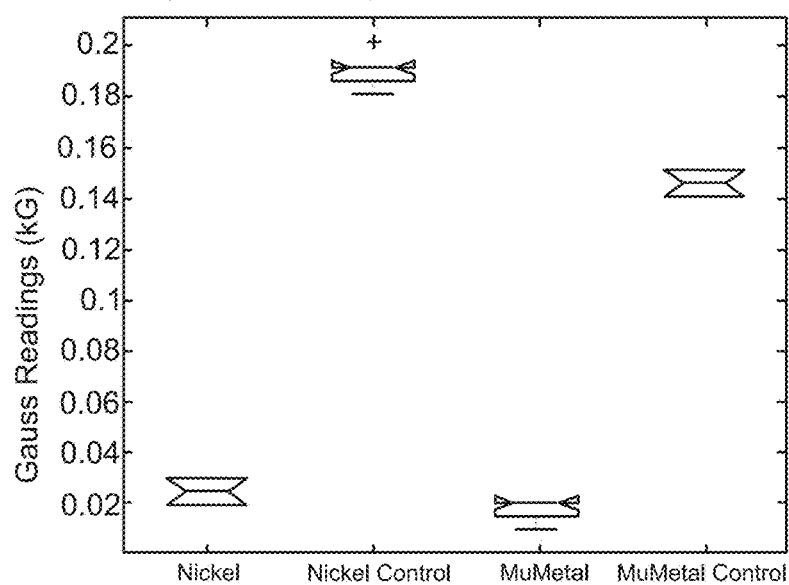

7.5 Results:

The results of the mag-shield testing with copper are shown in FIG. 17. It is clear that the copper foil played a large role in deflecting the magnitude of the magnetic field picked up by the gaussmeter. By examining the median values taken with the shielding and with the control, the shielding passed the original acceptance criteria with approximately 83% reduction of the mag-field. Then during the second version of the test where Nickel and Mu-Metal were tested, the results showed a 93% reduction of a magnetic field again passing the test criteria.

7.6 Conclusion:

From the results, the team concludes that Nickel and MuMetal are effective as magnetic shielding elements with regards to the proposed device. The initial acceptance criteria were met and exceeded by each shielding element in its respective test. The Nickel has an average Mag Field reduction of 84%, and results from MuMetal readings gave between 85-93% Mag Field reduction. This trend between the two materials follows the original supposition that MuMetal would perform better than Nickel due to its higher magnetic permeability.

8.0 Magnetic Pull Force

8.1 Purpose:
The purpose of examining this problem was to see whether the concentric ring magnet setup would remain together when subjected to the inertial force from rapidly traverse from the distal orientation to proximal during the pulsatile oscillations within the heart.

8.2 Acceptance Criteria:
The force holding the two ring magnets to each other must be at least 2 orders of magnitude greater than the inertial force that the magnets are subjected to by the impulse caused by sudden change in direction.

8.3 Overview:
Proof of concept research and hand calculations will be conducted in order to ensure that the magnetic force is greater than the inertial force of the inner magnet.

8.4 Background:
Two concentric ring magnets (with a tightly wound copper coil in between them) are oscillated up and down a linear track. The goal of this motion is to induce an electromagnetic field. The proposed device will be placed within a heart chamber that has a beat frequency of 1 Hz. The inner magnet must be able to stay within the larger outer magnet at the top and bottom of the periodic oscillations. In order for the inner magnet to stay in place, the force due to its inertia must not overcome the force between the magnets themselves.

8.5 Methods:
The primary equation than describes the impulse of a moving object is as follows:

$$F = m\frac{\Delta v}{t} \quad (8.1)$$

where F is the force, m is the mass of the object, $\Delta v$ is the change in velocity, and t is the time of impulse. In this particular application, two 3× scale ring magnets were used. Both were N52 grade neodymium ring magnets. The larger outer magnet had specifications: 1" OD×½" ID×⅛" thick. The smaller inner magnet had specifications ½" OD×¼" ID×⅛" thick. The pull force rating for the big and small magnets was 11.2 and 6.6 pounds of force respectively.

Doing the calculation, m is the mass of the magnet setup, which is 2.26 g. T is the time it takes for each oscillation is approximately 0.5 seconds. V is equal to the distance the magnets travel divided by the time it takes for them to travel; the distance traveled is taken from the scale model, which is 28 mm, and the time is equal to half a second.

8.6 Results:
Applying the impulse equation and the information we have; we get that the inertial force due to impulse on the system is equal to approximately $5.69*10^{-6}$ pounds of force.

8.7 Conclusion:
This force is more than 2 orders of magnitude less than the force of the larger magnet, which was 11.2 pounds of force. Thus, the experiment passes the original acceptance criteria.

9.0 Animal Study

9.1 Purpose:
To test if the proposed device could reasonably fit inside the ventricle of a heart, a pig's heart was obtained, and different 3D models were inserted. The dimensions of the device must be designed to fit inside the heart because otherwise, a large device could disrupt heart function potentially harm patients.

9.2 Acceptance Criteria:
The device should reasonably fit inside the heart without stretching or ripping the muscle fibers.

9.3 Overview:
4 models were tested inside the heart: solid shell, four strip shell, chubby, and two times scale model. The solid shell, four strip shell, and chubby models all passed the acceptance criteria: they easily fit into both the left and the right ventricles of the heart. The two times scale model did not pass the acceptance criteria as it was too large.

9.4 Background:
The heart is made of four chambers, the atriums (right/left) and the ventricles (right/left). Atriums act to receive blood from either the body (right) or from the lungs (left) while the ventricles send this blood out to the body(left) or the lungs(right) to be oxygenated. Here the left ventricle is measured for its size and volumetric capabilities to store an energy harvesting device.

9.5 Materials:
The models were designed on Solidworks 2018 and 3D printed with an IIIP 3D printer with PLA filament. While the pig heart was supplied from a local H-mart.

9.6 Methods:
The top half of the pig's heart was cut and removed. Each model was then inserted into the open left and right ventricles to test the dimensions. Then the same pig's heart was inserted in the heart pumping fixture a twisting motion was performed by hand to visualize how the device would work. Afterward, the pig heart was examined for the inner dimensions for future reference.

Figure 18:
Figure 18:
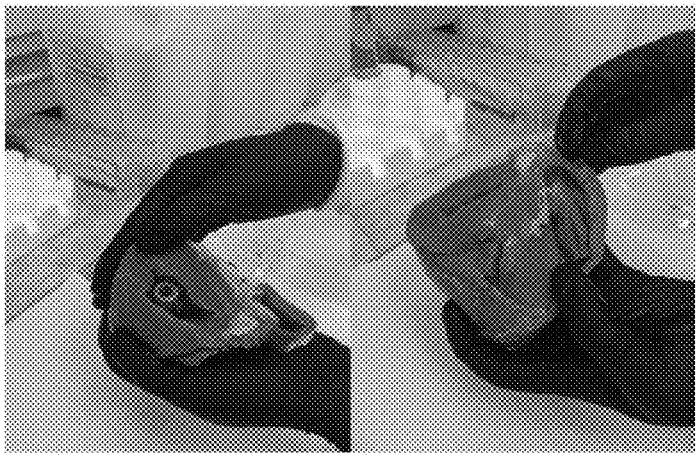

9.7 Results:
When inserted into the left ventricle of the pig's heart, the solid shell, four strip shell, and the chubby models all fit with ease. The model and the muscles walls made contact but the device easily slid into the chamber. The two times scale model could technically be inserted into the left ventricle. However, a great force was needed and the muscle fibers were stretched and started ripping. In addition, the two times model could not be inserted fully length-wise. This confirmed the feasibility of our prior set dimensions. FIG. 18 provides animal study result pictures.

TABLE 11

Dimensions of a Pig's Heart (Left Ventricle) diagram of the four chambers of the heart.

| Dimension (Descending) | Value [cm] | Description |
| --- | --- | --- |
| 1 | 2 | Pulmonary Valve Diameter |
| 2 | 9 | Pulmonary Valve to outer wall |
| 3 | 4.5 | Left Ventricle |
| 4 | 3.5 | Left Ventricle |
| 5 | 4 | Left Ventricle |
| 6 | 3 | Left Ventricle |
| 7 | 2 | Left Ventricle |
| 8 | 0.7 | Apex |

9.8 Conclusion:
The one scale models passed the acceptance criteria and the team obtained valuable data of dimensional accuracy. Although it must be noted that a big heart is notably larger than a human heart, as a rough prototype, it showed that the device size was plausible.

10.0 Electromagnetic Thermal Analysis

10.1 Purpose:
Because the FDA regulates that a medical device cannot raise the temperature of the surrounding tissue more than 2°

C., this test serves to demonstrate whether the heat and temperature increase from the friction of the magnets rubbing on the device will meet that criteria.

10.2 Acceptance Criteria:

The temperature probe inside the device with sprayed water over it should not exceed 39° C., 2° C. above body temperature.

10.3 Overview:

The FDA requires all implantable devices to stay within 2° C. (+/−) of body temperature, 39° C., to ensure the safety of the patient. In order to investigate the issue of thermal increases due to friction forces in the oscillating magnet system, a simple experiment was designed, and data was compared to the 39° C. upper thermal limit dictated by the FDA. Results found that while a control test saw a ~5-7° C. temperature change, the same test run with water temperature water as a coolant saw smaller changes in comparison. In all three water test trials, the temperatures did not exceed 2° C. from the initial measurement.

Figure 19:
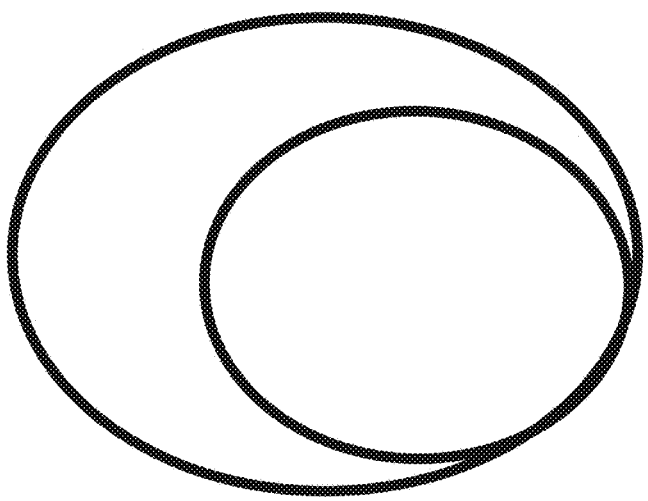
FIG. 19. Electromagnetic Thermal Testing—Root Cause. A basic figure showing the underlying problem with the double magnet system where one magnet would continue to rub against the other, sparking the initial concern and need for the study.

10.4 Background:

During experimentation, it was noted that the magnets were unable to maintain an optimum concentricity and thus the inner magnet continually moved toward one side. This of course was a point of concern particularly for heat generation caused by the friction of the two surfaces. This phenomena is detailed in FIG. 19 underlines the issue. FIG. 19 is a basic figure that shows the underlying problem with the double magnet system where one magnet would continue to rub against the other, sparking the initial concern and need for the study.

10.5 Materials:

For the heat generation testing, three main materials were used: PDMS, two concentric magnets, and a thermocouple. In order to set up the experiment, a 3D-printed hollow cylinder was used that was made to fit the outer diameter of the inner magnet, with an inner diameter of ¹³⁄₁₆" and an outer diameter of ¹⁵⁄₁₆". Two 3× scale ring magnets were used. Both were N52 grade neodymium ring magnets. The larger outer magnet had specifications: 1" OD×½" ID×⅛" thick. The smaller inner magnet had specifications ½"OD× ¼" ID×⅛" thick. A thin layer of PDMS of 0.75" surrounded the 3D printed cylinder. An outer magnet was positioned to fit around the PDMS layer and the cylinder. The thermocouple was placed on one end in between the PDMS layer and the cylinder and was secured using electrical tape.

For the water testing, a similar list of materials was used in addition to a 6 L/min peristaltic pump and a hot plate to pump the water and maintain the temperature at around body temperature.

10.6 Methods:

The control setup of the experiment was primarily just testing the heat generated from the magnets against the PDMS. The outer and inner magnets were oscillated manually across the height of the hollow cylinder for 15 minutes. The thermocouple acquired the temperature change throughout the time frame. Three trials were conducted per the control (without water) and variable (with water).

Similar to the control setup, the trials with water were conducted by manually oscillating the inner and outer magnets over the PDMS covered cylinders for 15 minutes. A thermocouple was placed under the PDMS surface of the cylinder and in the water tank and the temperature was recorded throughout the trial. A 1000 mL beaker filled with water was maintained at a temperature of 38° C. using a hot plate. Warm water was pumped from the beaker at 100 mL/min and sprayed over the manually oscillating magnet-cylinder setup. More warm water was periodically added to the beaker as the trial went on to keep the temperature constant.

Figure 20:
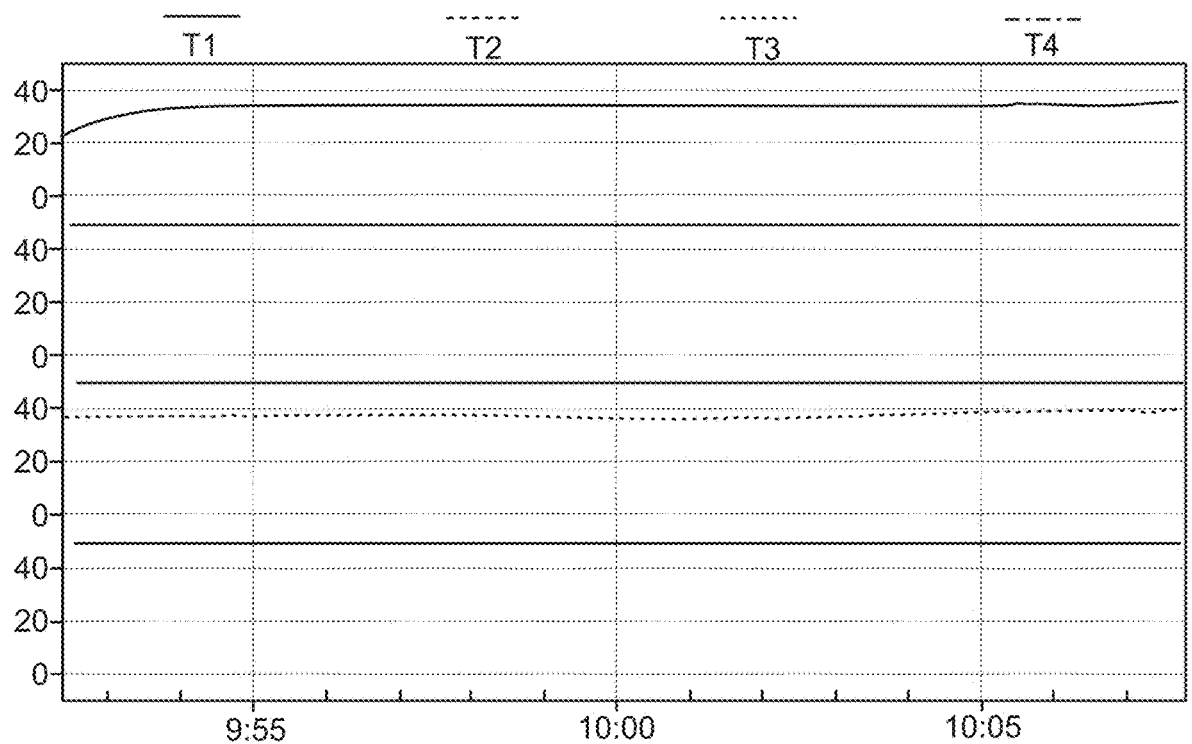
FIG. 20. Temperature Testing Benchtop Results. Displayed here are the data from one of the tests with the 6 L/min pump. Water was stored at a constant body temperature shown in green (or T3) and the surface temperature (T1), little to no temperature fluctuations are seen during the trials.

10.7 Results:

From the control experiment, the change in temperature ranged from 5-7° C. The first run started at 23.4° C. and increased to 29.1° C. after 15 minutes, resulting in a 5.6° C. temperature change. FIG. 20 and Tables 12-13 show the change in temperature for each of the four runs with its starting temperature and ending temperature after 15 minutes. Calculating the average change in temperature during the control (with no water) would be 6.06° C. While with water the temperature dropped to acceptable levels of 1.1° C. change in temperature. Of course, the question must raise if 15 minutes would be a long enough time to determine if the system had reached equilibrium. However, by viewing the output graphs from the thermocouple, after initially heating from room temperature, the surface temperature quickly reaches equilibrium and only slightly if at all alters.

TABLE 12

Temperature Testing Control Variable Results (No Water)

| Run | Starting Temperature ° C. | Ending Temperature ° C. | Change in Temperature ° C. |
|---|---|---|---|
| 1 | 23.4 | 29.1 | 5.6 |
| 2 | 23.6 | 30.4 | 6.8 |
| 3 | 24 | 29.8 | 5.8 |

TABLE 13

Temperature Testing Variable Results (6 L/min Water)

| Run | Starting Temperature ° C. | Ending Temperature ° C. | Change in Temperature ° C. |
|---|---|---|---|
| 1 | 29.9 | 31.4 | 1.5 |
| 2 | 33.4 | 35.1 | 1.7 |
| 3 | 34.6 | 34.7 | 0.1 |

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

[1] K. G. Tarakji, C. R. Ellis, P. Defaye, and C. Kennergren, "Cardiac Implantable Electronic Device Infection in Patients at Risk," Arrhythmia Electrophysiol. Rev., vol. 5, no. 1, p. 65, 2016.

[2] M. A. Karami, D. J. Inman, and M. Amin Karami, "Powering pacemakers from heartbeat vibrations using linear and nonlinear energy harvesters Modeling and experimental verification of a fan-folded vibration energy harvester for leadless pacemakers Powering pacemakers from heartbeat vibrations using linear," Appl. Phys. Lett., vol. 100, no. 101, pp. 42901-41301, 2012.

[3] M. H. Ansari and M. Amin Karami, "Modeling and experimental verification of a fan-folded vibration energy harvester for leadless pacemakers," J. Appl. Phys., vol. 119, no. 100, 2016.

[4] https://www.cdc.gov/dhdsp/data statistics/fact sheets/fs atrial fibrillation.htm
[5] Donald McLean, John Saunders, "Biologically Implantable and Energized Power SuppM", 3563245, 1971
[6] Afraanz Irani, Mark Bianco, David Tran, Peter Deyoung, Melanie Wyld, Tony Li, 'Energy Generating Systems for Implanted medical Devices' 0171404, 2009.
[7] Sanjay Kotha, T. Sundarshan, R. Radharkishnun, "Magnetic Fluid Power Generator and Method for Generating Power," 6982501, 2006.
[8] D. P. Arnold and S. Cheng, "Method and apparatus for motional/vibrational energy harvesting via electromagnetic induction using a magnet array," 0187207, 2015.
[9] D. J. Inman, M. Amin Karami, D. J. Bradley, "Piezoelectric Vibrational Energy Harvester," 0365018, 2015.
[10] W. D. Fremont, "Corrosion Resistance and Biocompatibility of Passivated NiTi," 2000.
[11] M. F. Khan, "Design Optimisation fir Stent Manufacture," *University of Nottingham*. April, 2018.
[12] K. X. Qian and H. X. Xu, "Gyro-Effect and Earnshaw's Theorem: Stable and Unstable Equilibrium for Rotary acid Stationary Permanent Magnetic Levitators," 2008 2nd international Conference on Bioinformatics and Biomedical Engineering, Shanghai, 2008, pp. 1323-1325. doi: 10.1 109/ICBBE.2008.659
[13] Koehler, Kenneth R. College Physics for Students of Biology and Chemistry. Cincinnati, Ohio: Raymond Walters College University of Cincinnati, 1996: Chapter 3, Fluids: Human Cardiovascular System.
[14] S. Pal, "Design of artificial human joints & organs," Des. Artif. Hum. Joints Organs, vol. 9781461462552, pp. 1-419, 2014.
[15] M. H. Moosavi, N. Fatouraee, H. Katoozian, A. Pashaei, O. Camara, and A. F. Frangi, "Numerical simulation of blood flow in the left ventricle and aortic sinus using magnetic resonance imaging and computational fluid dynamics," Computer Methods in Biomechanics and Biomedical Engineering, vol. 17, no. 7. Taylor & Francis, pp. 740-749, 2014.
[16] V. P. Shastri, "Non-Degradable Biocompatible Polymers in Medicine: Past, Present, Future," Current Pharmaceutical Biotechnology, vol. 4, pp 331-337, 2003.

What is claimed is:

1. A recharging system for recharging batteries or providing power to an implantable device, the recharging system comprising:
   an electric coil adapted to be coupled to the implantable device, the electric coil defining a coil interior and a coil exterior;
   a magnetic component coupled to the electric coil and adapted to at least partially surround the implantable device;
   a mechanical actuator attached to the magnetic component, the mechanical actuator converting compression motion into motion of the magnetic component relative to the electric coil;
   an outer ring-shaped magnet positioned around the coil exterior, the outer ring-shaped magnet being translatable in a lengthwise direction between a first position and a second position about the electric coil and the implantable device when the recharging system is attached to the implantable device; and
   an inner ring-shaped magnet positioned in the coil interior, the inner ring-shaped magnet being magnetically coupled to the outer ring-shaped magnet such that translation of the outer ring-shaped magnet induces translation of the inner ring-shaped magnet.

2. The recharging system of claim 1, wherein the implantable device comprises a pacemaker, a gastric stimulation device, a defibrillator, a neurostimulator, a diaphragm pacing device, or a cochlear implant.

3. The recharging system of claim 1, wherein the mechanical actuator contacting the outer ring-shaped magnet, the mechanical actuator converting compression motion into linear motion that translates the out ring-shaped magnet along the lengthwise direction.

4. The recharging system of claim 3, wherein the outer ring-shaped magnet and the inner ring-shaped magnet are each independently composed of neodymium.

5. The recharging system of claim 3 wherein the outer ring-shaped magnet oscillates between the first position and the second position.

6. The recharging system of claim 3 wherein muscle contractions provide a force for moving the outer ring-shaped magnet along the lengthwise direction.

7. The recharging system of claim 3 wherein the mechanical actuator includes a mesh balloon that converts sideways compression into a lengthwise translation of the outer ring-shaped magnet.

8. The recharging system of claim 7 wherein the mesh balloon is a tube-shaped structure with a bulging central region.

9. The recharging system of claim 7 wherein the mesh balloon comprises a flexible shape-memory alloy.

10. The recharging system of claim 1, wherein the electric coil is coupled to an electric circuit configured to store electric energy generated in the electric coil, the electric circuit including a capacitor configured to store the electric energy.

11. A recharging system for recharging batteries or providing power to an implantable device, the recharging system comprising:
    an electric coil adapted to be coupled to the implantable device, the electric coil defining a coil interior and a coil exterior;
    an outer ring-shaped magnet positioned around the coil exterior, the outer ring-shaped magnet being translatable in a lengthwise direction between a first position and a second position about the electric coil and the implantable device when the recharging system is attached to the implantable device;
    an inner ring-shaped magnet positioned in the coil interior, the inner ring-shaped magnet being magnetically coupled to the outer ring-shaped magnet such that translation of the outer ring-shaped magnet induces translation of the inner ring-shaped magnet; and
    a mechanical actuator contacting the outer ring-shaped magnet, the mechanical actuator converting compression motion into linear motion that translates the out ring-shaped magnet along the lengthwise direction.

12. The recharging system of claim 11 wherein the outer ring-shaped magnet oscillates between the first position and the second position.

13. The recharging system of claim 11 wherein muscle contractions provide a force for moving the outer ring-shaped magnet along the lengthwise direction.

14. The recharging system of claim 11 wherein the mechanical actuator includes a mesh balloon that converts sideways compression into a lengthwise translation of the outer ring-shaped magnet.

15. The recharging system of claim 14 wherein the mesh balloon is a tube-shaped structure with a bulging central region.

16. The recharging system of claim 14 wherein the mesh balloon comprises a flexible shape-memory alloy.

17. The recharging system of claim 11, wherein a type and winding of the electric coil is selected based on a desired electric energy.

* * * * *